(12) United States Patent
Bonomo et al.

(10) Patent No.: US 10,251,869 B2
(45) Date of Patent: *Apr. 9, 2019

(54) COMPOSITIONS AND METHODS OF INHIBITING METALLO-β-LACTAMASES

(71) Applicant: CASE WESTERN RESERVE UNIVERSITY, Cleveland, OH (US)

(72) Inventors: Robert Bonomo, Cleveland, OH (US); Alejandro Jose Vila, Sante Fe (AR); S. Graciela Mahler, Montevideo (UY)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/463,952

(22) Filed: Mar. 20, 2017

(65) Prior Publication Data

US 2017/0252326 A1 Sep. 7, 2017

Related U.S. Application Data

(63) Continuation of application No. 14/694,550, filed on Apr. 23, 2015, now Pat. No. 9,597,319.

(60) Provisional application No. 61/983,229, filed on Apr. 23, 2014.

(51) Int. Cl.
*A61K 31/429* (2006.01)
*A61K 31/407* (2006.01)

(52) U.S. Cl.
CPC .......... *A61K 31/429* (2013.01); *A61K 31/407* (2013.01)

(58) Field of Classification Search
CPC ... A61K 31/431; A61K 31/429; A61K 31/426
USPC .......................................... 548/154; 514/368
See application file for complete search history.

(56) References Cited

U.S. PATENT DOCUMENTS

| 7,115,641 | B2* | 10/2006 | Merianos | A01N 47/12 514/375 |
| 9,976,170 | B2* | 5/2018 | Fernandez Garcia | C12Q 1/689 |
| 2010/0240800 | A1* | 9/2010 | Cunningham | A01K 1/0157 523/122 |
| 2011/0118323 | A1* | 5/2011 | Luesch | C07D 513/18 514/366 |
| 2011/0269817 | A1* | 11/2011 | Sassone-Corsi | A61K 31/00 514/44 A |
| 2012/0329842 | A1 | 12/2012 | Song et al. | |
| 2013/0281359 | A1 | 10/2013 | Maiti et al. | |
| 2014/0296310 | A1 | 10/2014 | Alex et al. | |
| 2014/0364385 | A1* | 12/2014 | Bugni | C07D 513/18 514/31 |
| 2018/0042900 | A1* | 2/2018 | Serbus | A61K 31/4184 |

FOREIGN PATENT DOCUMENTS

| CN | 101723961 A | * | 6/2010 | |
| GB | 2460882 A | * | 12/2009 | G01N 33/558 |
| WO | WO-2009026544 A1 | * | 2/2009 | C07D 499/68 |
| WO | WO-2014191109 A1 | * | 12/2014 | A61K 31/5377 |

OTHER PUBLICATIONS

Szabo et al. Science of the Total Environment (2016) 551-552, 393-403. (Year: 2016).*
Abdullah G.M. Al-Sehemi JKAU: Sci., vol. 21(1), pp. 79-88 (2009) (Year: 2009).*
A.S. Dajani The Journal of International Medical Research 29: 257-269 (2001) (Year: 2001).*
Cook et al. Chemistry of Penicillin. Chapter XXV "Thiazolidines", pp. 921-972 (1949) (Year: 1949).*
Saiz, Cecilia, et al., "Discovering Echinococcus granulosus thioredoxin glutathione reductase inhibitors through site-specific dynamic combinatorial chemistry", Mol Divers 2014.

* cited by examiner

*Primary Examiner* — Nyeemah A Grazier
(74) *Attorney, Agent, or Firm* — Tarolli, Sundheim, Covell & Tummino LLP

(57) ABSTRACT

A method of treating a bacterial infection in a subject in need thereof includes administering to the subject therapeutically effective amounts of at least one β-lactam antibiotic and at least one bisthiazolidine metallo-β-lactamase inhibitor.

19 Claims, 8 Drawing Sheets

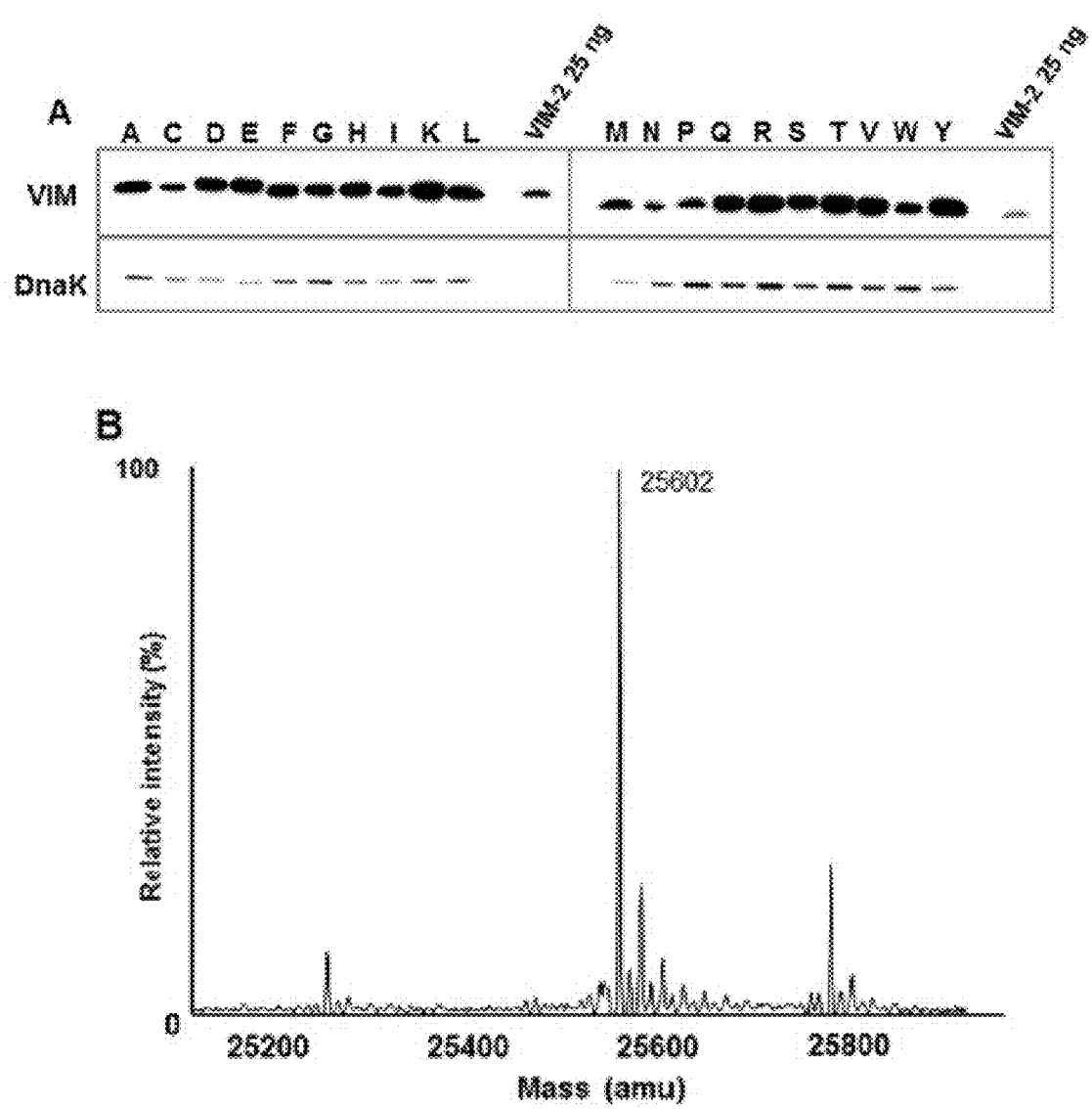
Figs. 3A-B

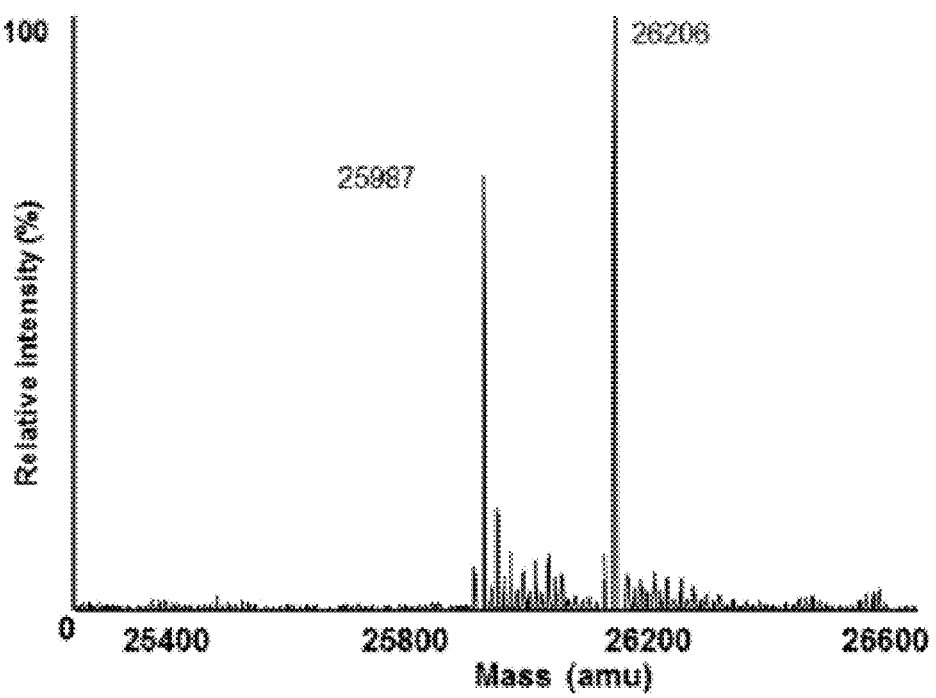
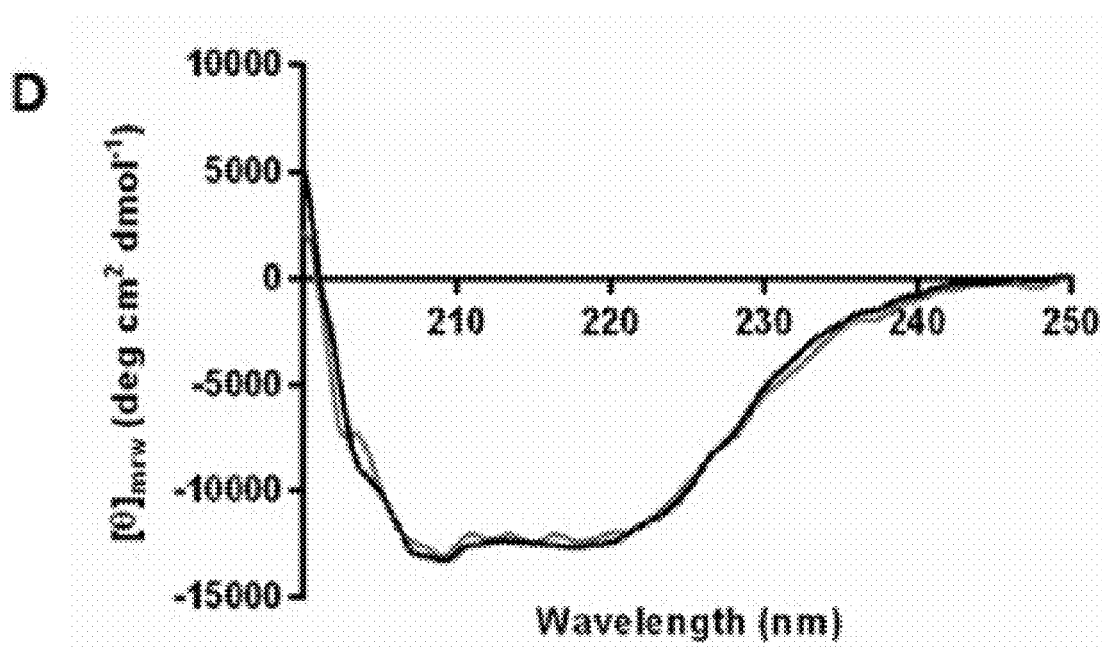
Figs. 3C-D

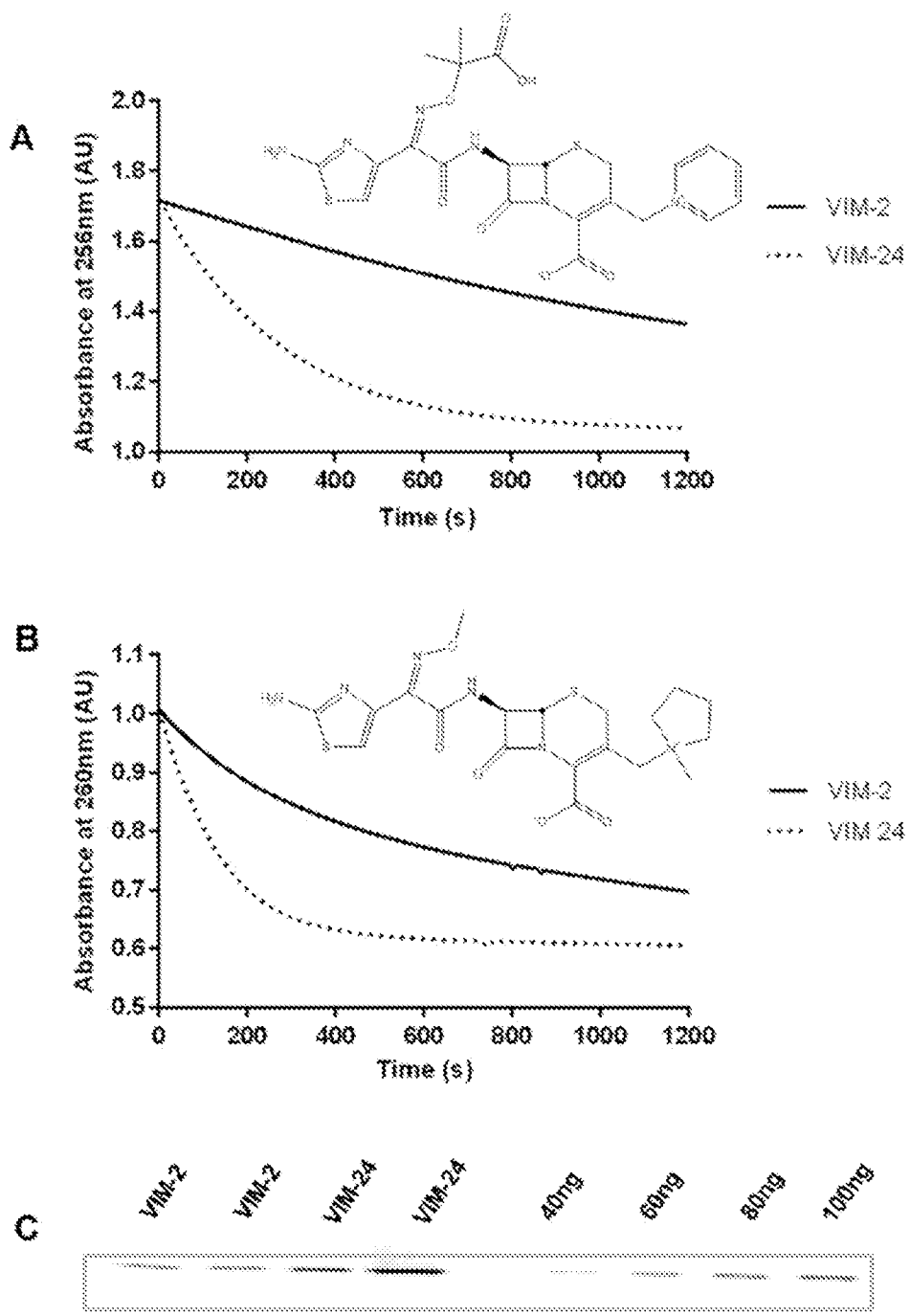
Figs. 4A-C

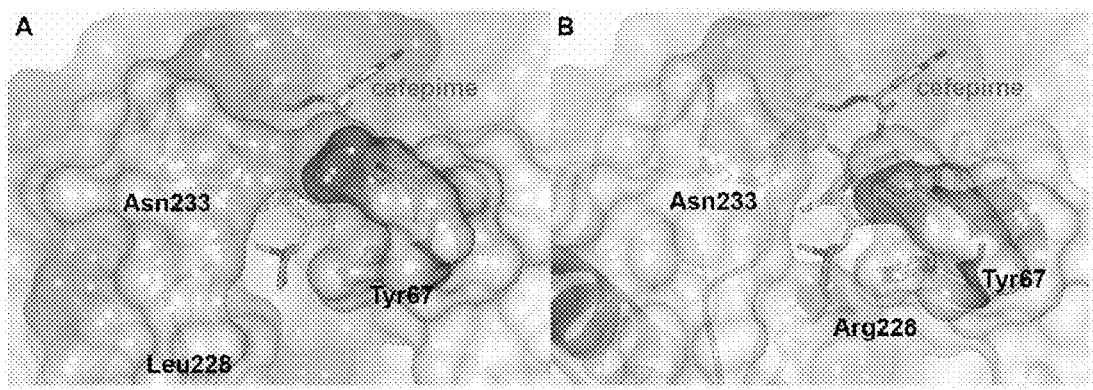
Figs. 5A-B
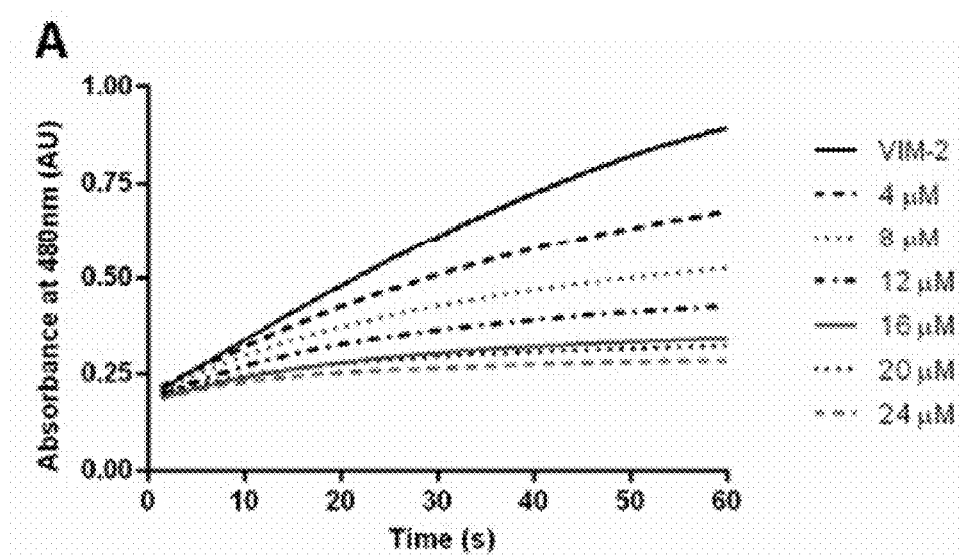
Fig. 6A

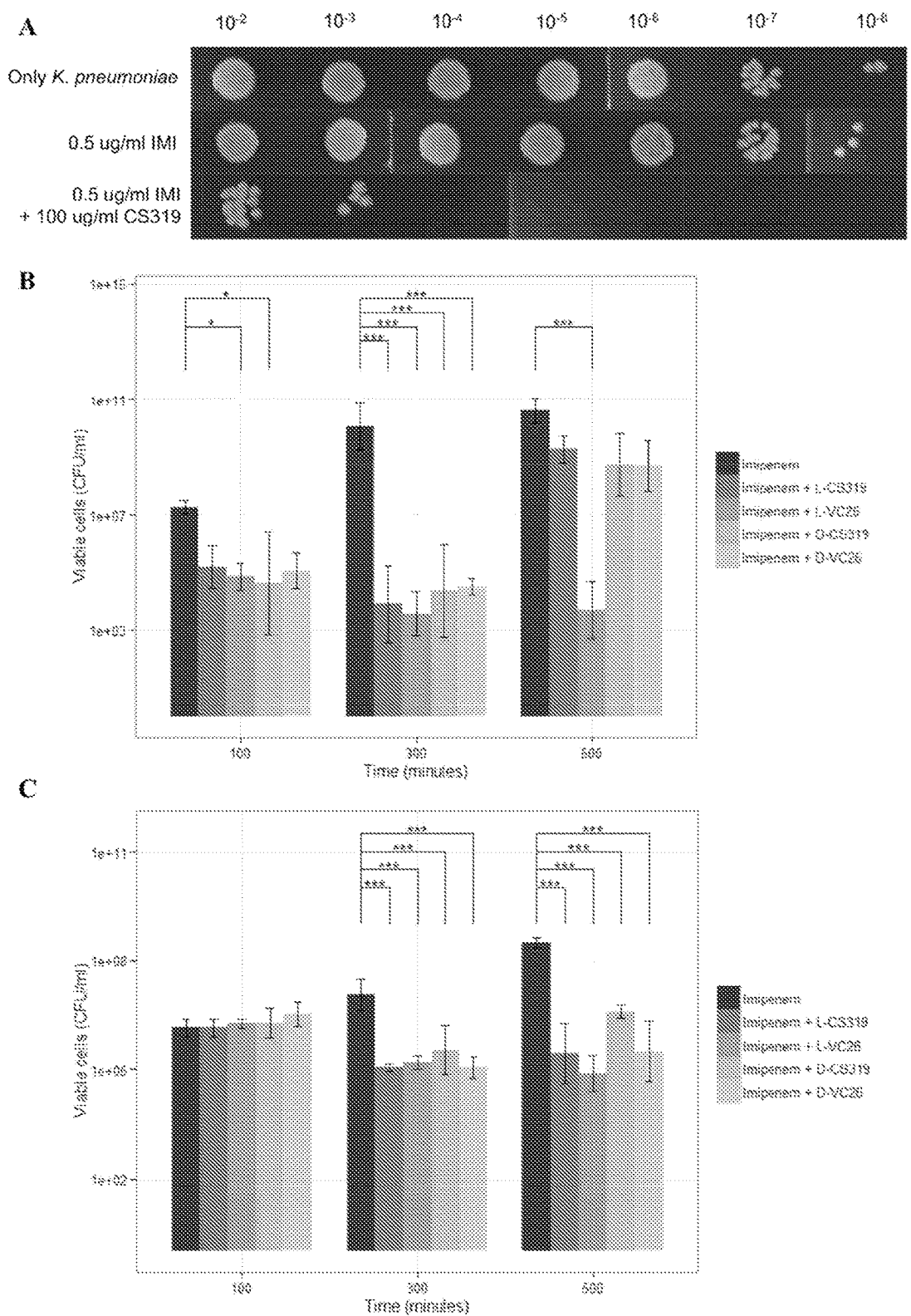
Figs. 7A-C

COMPOSITIONS AND METHODS OF INHIBITING METALLO-β-LACTAMASES

RELATED APPLICATION

This application claims priority from U.S. Provisional Application No. 61/983,229, filed Apr. 23, 2014, the subject matter of which is incorporated herein by reference in its entirety.

GOVERNMENT FUNDING

This invention was made with government support under Grant No. AI100560 awarded by The National Institutes of Health. The United States government has certain rights to the invention.

BACKGROUND

Carbapenems are the most potent β-lactam antibiotics. In many instances, these lifesaving drugs are considered "last line agents" due to their activity against many antibiotic resistant Gram-negative bacteria. Unfortunately, carbapenem-resistant bacteria are rapidly emerging as a cause of opportunistic healthcare-associated infections, particularly in immunocompromised individuals. As a result, antimicrobial treatment of these carbapenem-resistant pathogens is becoming limited. Widespread dissemination of carbapenem-resistant Gram-negative bacteria presents a profound challenge to effective healthcare.

Production of hydrolytic enzymes (β-lactamases) is a key mechanism of β-lactam resistance in Gram-negative bacteria. For a long time, carbapenem-hydrolyzing β-lactamases (carbapenemases) were infrequent. There are two types of β-lactamases with carbapenemase activity: those that use a serine residue as the nucleophile to inactivate the antibiotic (i.e., serine carbapenemases), and those that use $Zn^{2+}$ ions to activate a nucleophilic water molecule (i.e., metallo-β-lactamases, MBLs).

MBLs are the most potent carbapenemases. MBLs are broad spectrum enzymes, being able to hydrolyze equally well penicillins and cephalosporins (FIG. 1). In the 1980s to 1990s, only a few MBLs were known, and these were limited to strains of restricted clinical impact. However, MBLs are now increasingly encountered in important Gram-negative pathogens, including Enterobacteriaceae and non-fermenting species. Multiple MBLs have been found on mobile genetic elements and have consequently disseminated worldwide among pathogenic and opportunistic bacteria. For instance, variants of the NOM, IMP and VIM MBLs are now globally distributed, SPM-1 is present in *Pseudomonas aeruginosa* across South America, and has recently been identified in Europe.

In particular, NDM-1, is raising significant concern because: i) it is located in a mobile genetic background with multiple resistance elements; ii) it is becoming prevalent in Enterobacteriaceae; and iii) it has now been identified in food and water-borne pathogens, such as *Vibrio* and *Shigella* Spp. NDM-1 producing isolates have already been identified that are resistant to all antibiotics except colistin and tigecycline.

Inhibitors for MBLs are not yet commercially available. MBL-mediated hydrolysis does not involve a covalent acyl-enzyme intermediate, which is in contrast with the hydrolytic mechanism of serine β-lactamases. Thus, the strategy of generating stable acyl-enzyme analogues which has provided inhibitors for the serine enzymes is not applicable to MBLs. In contrast to the serine carbapenemases, there is no MBL inhibitor in clinical development. The structural variability present among MBLs has prevented generalizations regarding substrate binding and hydrolysis, thus hampering the development of effective inhibitors.

Despite sharing a common 3D fold, MBLs exhibit significant sequence diversity. This diversity has led to the definition of 3 MBL subclasses (B1, B2 and B3) varying in the arrangement of metal ligands in the active site structure, zinc stoichiometry, loop architecture and their activity with respect to different β-lactams. Consequently, while numerous groups have evaluated a wide variety of scaffolds as potential MBL inhibitors, variation between MBLs, even in the same Subclass, results in differences in inhibitor potency of several orders of magnitude.

SUMMARY

Embodiments described herein relate to compositions and methods of inhibiting carbapenemase or carbapenem-hydrolyzing β-lactamase activity as well as to compositions and methods of treating bacterial infections, such as carbapenem resistant gram negative bacterial infections, in a subject in need thereof. It was found that bisthiazolidines can be used to inhibit and/or inactivate carbapenemase or carbapenem-hydrolyzing β-lactamase activity, and particularly, metallo-β-lactamase enzymatic function. The inhibition of metallo-β-lactamase enzymatic function through a two-step process wherein an initial enzyme (E)-inhibitor (I) complex (EI) undergoes a conformational transition to a more stable species, E*I. The bisthiazolidine metallo-β-lactamase inhibitors are therefore useful in the treatment of bacterial infections in subjects in need thereof alone or in combination with β-lactam antibiotics and/or with other non-β-lactam antibiotics.

In some embodiments, therapeutically effective amounts of a bisthiazolidine or fused oxazolidine metallo-β-lactamase inhibitor can be administered in combination with a β-lactam antibiotic to treat a β-lactam resistant bacterial infection in a subject in need thereof. The bisthiazolidine metallo-β-lactamase inihibitor can include at least one compound having the formula:

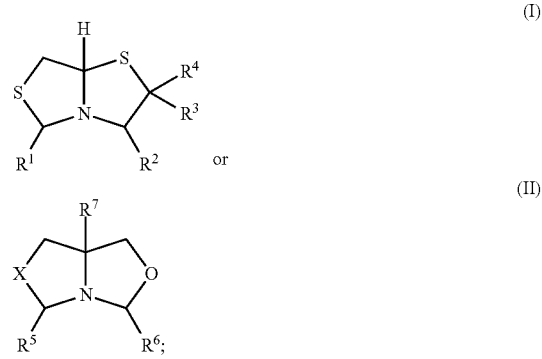

wherein x is O or S, $R^1$ is selected from the group consisting of a substituted or unsubstituted $C_1$-$C_{12}$ alkylthio, $C_1$-$C_{12}$ alkyldithio, $C_1$-$C_{12}$ alkylsulfonyl, and $C_1$-$C_{12}$ alkylsulfate, $R^2$ is selected from the group consisting of H, a substituted or unsubstituted carboxy, $C_1$-$C_{12}$ alkyl, $C_1$-$C_{12}$ alkenyl, carboxylato, carbamoyl, $C_1$-$C_{12}$ alcohol, $C_1$-$C_{12}$ alkoxycarbonyl, $C_1$-$C_5$ alkylcarbonato, $C_1$-$C_5$ alkyl-carbamoyl, and hydroxyaminocarbonyl, $R^3$ and $R^4$ are each independently selected from the group consisting of a H, a $C_1$-$C_{12}$ alkyl, and $C_1$-$C_{12}$ alkenyl, and wherein $R^2$ and $R^3$ may be linked to form a cyclic or polycyclic ring, $R^5$ is selected from the group consisting of a substituted or unsubstituted $C_1$-$C_{12}$ alkylthio, $C_1$-$C_{12}$ alkyldithio $C_1$-$C_{12}$ alkylsulfonyl, and $C_1$-$C_{12}$ alkylsulfate;

$R^6$ and $R^7$ are each independently selected from the group consisting of H, a substituted or unsubstituted carboxy, $C_1$-$C_{12}$ alkyl, carboxylato, carbamoyl, $C_1$-$C_{12}$ alcohol, $C_1$-$C_{12}$ alkoxycarbonyl, $C_1$-$C_{12}$ alkylcarbonato, $C_1$-$C_{12}$ alkyl-carbamoyl, and hydroxyaminocarbonyl; and pharmaceutically acceptable salts thereof.

In some embodiments, the bacterial infection can be a carbapenem resistant gram negative bacterial infection and the bisthiazolidine metallo-β-lactamase inihibitor can be administered to the subject at an amount effective to inhibit carbapenemase or carbapenem-hydrolyzing β-lactamase activity.

In other embodiments, the bisthiazolidine metallo-β-lactamase inihibitor can include at least one compound having the formula:

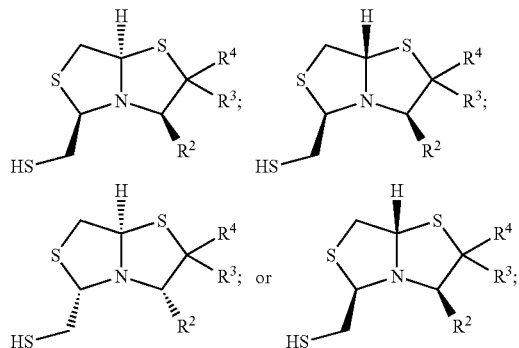

wherein $R^2$ is selected from the group consisting of H, a substituted or unsubstituted carboxy, $C_1$-$C_{12}$ alkyl, carboxylato, carbamoyl, $C_1$-$C_{12}$ alcohol, $C_1$-$C_{12}$ alkoxycarbonyl, $C_1$-$C_5$ alkylcarbonato, $C_1$-$C_5$ alkyl-carbamoyl, and hydroxyaminocarbonyl, $R^3$ and $R^4$ are each independently selected from the group consisting of a H, a lower alkyl, and wherein $R^2$ and $R^3$ may be linked to form a cyclic or polycyclic ring, and pharmaceutically acceptable salts thereof.

In still other embodiments, the bisthiazolidine metallo-β-lactamase inihibitor can include at least one compound having the formula:

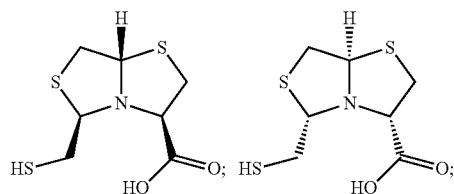

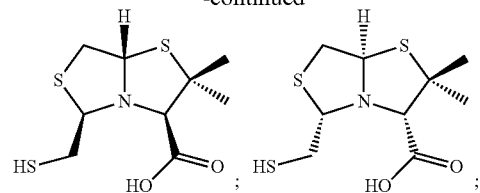

and pharmaceutically acceptable salts thereof.

In still other embodiments, the β-lactam antibiotic administered in combination with the bisthiazolidine metallo-β-lactamase inihibitor can include at least one of amoxicillin, ampicillin, azlocillin, mezlocillin, hetacillin, bacampicillin, carbenicillin, sulbenicillin, ticarcillin, piperacillin, mecillinam, methicillin, ciclacillin, oxacillin, cloxacillin, dicloxacillin, nafcillin, cephalothin, cephaloridine, cefaclor, cefadroxil, cefamandole, cefazolin, cephalexin, cephradine, ceftizoxime, cefoxitin, cephacetrile, cefotiam, cefotaxime, cefsulodin, cefoperazone, cefinenoxime, cefmetazole, cephaloglycin, cefonicid, cefodizime, cefpirome, ceftazidime, ceftriaxone, cefpiramide, cefozopran, cefepime, cefuzonam, cefpimizole, cefclidin, cefixime, ceftibuten, cefdinir, cefpodoxime axetil, cefpodoxime proxetil, cefteram pivoxil, cefetamet pivoxil, cefcapene pivoxil, cefditoren pivoxil, cefuroxime, cefuroxime axetil, loracarbacef, latamoxef, CXA-101, imipenem, meropenem, biapenem, panipenem, ertapenem, doripenem, aztreonam, carumonam, and pharmaceutically acceptable salts.

BRIEF DESCRIPTION OF THE DRAWINGS

FIGS. 4(A-C) illustrate plots and immunoblot showing hydrolysis of 500 μM of ceftazidime (A) and cefepime (B) was monitored at λ256 and λ260, respectively, using 70 nM of purified VIM-2 and VIM-24. Chemical structures of the substrates are shown in the upper right side of each plot. Production of VIM-2 and VIM-24 expressed in *E. coli* DH10B was assessed from periplasmic preparations by immunoblotting (C). Two independent periplasmic extractions are presented. A standard curve of purified VIM-2 was used to quantify the proteins from each preparation.

FIGS. 5(A-B) illustrate images showing interactions of cefepime with VIM-24 and VIM-2. Intact cefepime was manually docked into the model of VIM-24 and the complex minimized using the YASARA server. (A) The resulting orientation was superposed onto the crystal structure of native VIM-2 (PDB id 1KO3) using SSMSuperpose. (B) Note the steric clash between the N-methylpyrrolidine group at cefepime C3 and the guanidino side chain of VIM-2 Arg228.

FIGS. 7(A-C) illustrate BTZs restore the in vitro activity of imipenem against VIM-24 producing *K. pneumoniae* (A, B) and VIM-2 producing *P. aeruginosa* (C). A. Bacteria were grown at sublethal concentrations of imipenem alone (8 mg/L for *P. aeruginosa* and 0.5 mg/L for *K. pneumoniae*) or in combination with 100 mg/L of each BTZ. Viable cells were recovered at 100, 300 and 500 min. B-C. Results shown are the mean of three biological replicates+/-SD. Adjusted p-values are illustrated on the figures (*=0.05, =0.01, *=0.001).

DETAILED DESCRIPTION

Figure 1:
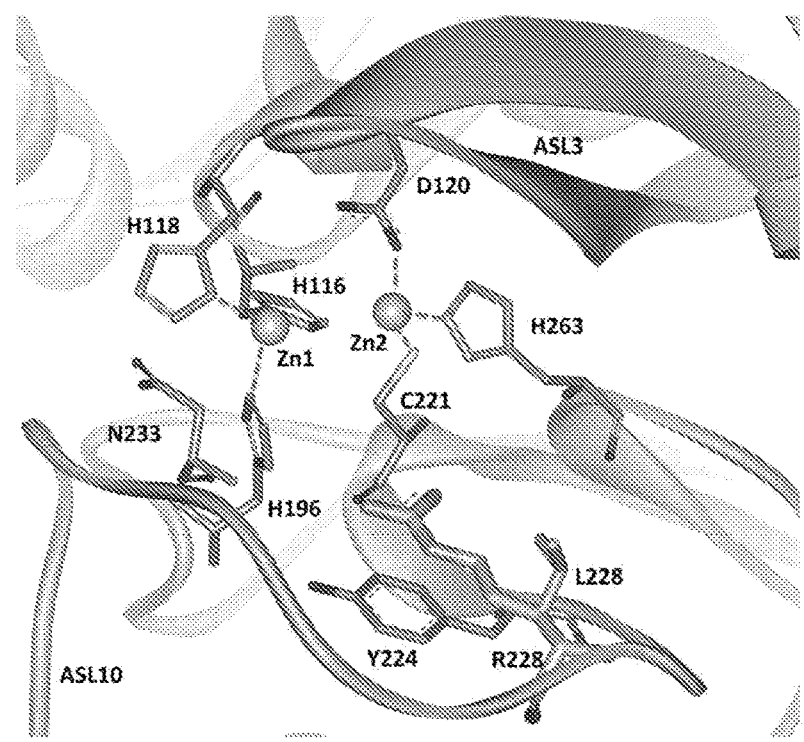
FIG. 1 illustrates a schematic drawing of an active site superimposition of VIM-2 (PDB ID 2YZ3) and VIM-24. Key residues in the active site are shown in sticks; position 228 (Arg; VIM-2); (Leu; VIM-24) is highlighted. Active Site Loops (ASL)-3 and -10 are shown. Zn2+ ions are represented as spheres.
Figure 2:
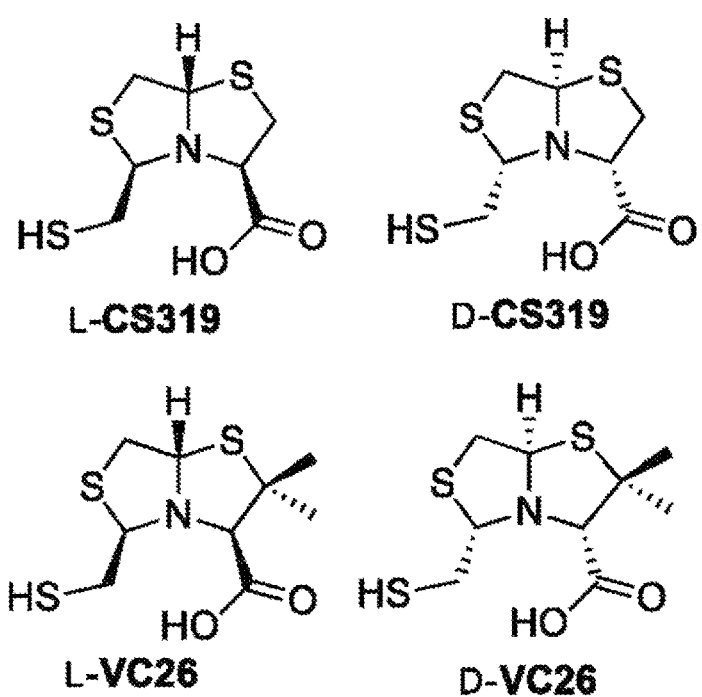
FIG. 2 illustrates chemical structures of Bisthiazolidine (BTZ) Inhibitors.

For convenience, certain terms employed in the specification, examples, and appended claims are collected here. Unless defined otherwise, all technical and scientific terms used herein have the same meaning as commonly understood by one of ordinary skill in the art to which this application belongs.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably.

The term "or" as used herein should be understood to mean "and/or", unless the context clearly indicates otherwise.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

It will be noted that the structure of some of the compounds of the application include asymmetric (chiral) carbon or sulfur atoms. It is to be understood accordingly that the isomers arising from such asymmetry are included herein, unless indicated otherwise. Such isomers can be obtained in substantially pure form by classical separation techniques and by stereochemically controlled synthesis. The compounds of this application may exist in stereoisomeric form, therefore can be produced as individual stereoisomers or as mixtures.

The term "isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center" whereas a sulfur bound to three or four different substitutents, e.g., sulfoxides or sulfinimides, is likewise termed a "chiral center".

The term "chiral isomer" means a compound with at least one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has 2n−1 enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Alternatively, when one or more chiral centers are present, a stereoisomer may be characterized as (+) or (−). Absolute configuration refers to the arrangement in space of the substituents attached to the chiral center. The substituents attached to the chiral center under consideration are ranked in accordance with the Sequence Rule of Cahn, Ingold and Prelog. (Cahn et al, Angew. Chem. Inter. Edit. 1966, 5, 385; errata 511; Cahn et al., Angew. Chem. 1966, 78, 413; Cahn and Ingold, J Chem. Soc. 1951 (London), 612; Cahn et al., Experientia 1956, 12, 81; Cahn, J., Chem. Educ. 1964, 41, 116).

The term "geometric Isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules. Further, the structures and other compounds discussed in this application include all atropic isomers thereof.

The term "atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

The terms "crystal polymorphs" or "polymorphs" or "crystal forms" means crystal structures in which a compound (or salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The term "derivative" refers to compounds that have a common core structure, and are substituted with various groups as described herein.

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrastemal injection and infusion.

The term "treating" is art-recognized and includes inhibiting a disease, disorder or condition in a subject, e.g., impeding its progress; and relieving the disease, disorder or condition, e.g., causing regression of the disease, disorder and/or condition. Treating the disease or condition includes ameliorating at least one symptom of the particular disease or condition, even if the underlying pathophysiology is not affected.

The term "preventing" is art-recognized and includes stopping a disease, disorder or condition from occurring in a subject, which may be predisposed to the disease, disorder and/or condition but has not yet been diagnosed as having it. Preventing a condition related to a disease includes stopping the condition from occurring after the disease has been diagnosed but before the condition has been diagnosed.

The term "pharmaceutical composition" refers to a formulation containing the disclosed compounds in a form suitable for administration to a subject. In a preferred embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, intranasal, inhalational, and the like. Dosage forms for the topical or transdermal administration of a compound described herein includes powders, sprays, ointments, pastes, creams, lotions, gels, solutions, patches, nebulized compounds, and inhalants. In a preferred embodiment, the active compound is mixed under sterile conditions with a pharmaceutically acceptable carrier, and with any preservatives, buffers, or propellants that are required.

The term "flash dose" refers to compound formulations that are rapidly dispersing dosage forms.

The term "immediate release" is defined as a release of compound from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of a compound from a dosage form over a prolonged period.

The phrase "pharmaceutically acceptable" is art-recognized. In certain embodiments, the term includes compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compounds of the application are capable of further forming salts. All of these forms are also contemplated herein.

"Pharmaceutically acceptable salt" of a compound means a salt that is pharmaceutically acceptable and that possesses the desired pharmacological activity of the parent compound. For example, the salt can be an acid addition salt. One embodiment of an acid addition salt is a hydrochloride salt. The pharmaceutically acceptable salts can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile being preferred. Lists of salts are found in Remington's Pharmaceutical Sciences, 18th ed. (Mack Publishing Company, 1990).

The compounds described herein can also be prepared as esters, for example pharmaceutically acceptable esters. For example, a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

The compounds described herein can also be prepared as prodrugs, for example pharmaceutically acceptable prodrugs. The terms "pro-drug" and "prodrug" are used interchangeably herein and refer to any compound, which releases an active parent drug in vivo. Since prodrugs are known to enhance numerous desirable qualities of pharmaceuticals (e.g., solubility, bioavailability, manufacturing, etc.) the compounds can be delivered in prodrug form. Thus, the compounds described herein are intended to cover prodrugs of the presently claimed compounds, methods of delivering the same and compositions containing the same. "Prodrugs" are intended to include any covalently bonded carriers that release an active parent drug in vivo when such prodrug is administered to a subject. Prodrugs are prepared by modifying functional groups present in the compound in such a way that the modifications are cleaved, either in routine manipulation or in vivo, to the parent compound. Prodrugs include compounds wherein a hydroxy, amino, sulfhydryl, carboxy, or carbonyl group is bonded to any group that may be cleaved in vivo to form a free hydroxyl, free amino, free sulfhydryl, free carboxy or free carbonyl group, respectively. Prodrugs can also include a precursor (forerunner) of a compound described herein that undergoes chemical conversion by metabolic processes before becoming an active or more active pharmacological agent or active compound described herein.

The term "protecting group" refers to a grouping of atoms that when attached to a reactive group in a molecule masks, reduces or prevents that reactivity. Examples of protecting groups can be found in Green and Wuts, Protective Groups in Organic Chemistry, (Wiley, 2.sup.nd ed. 1991); Harrison and Harrison et al., Compendium of Synthetic Organic Methods, Vols. 1-8 (John Wiley and Sons, 1971-1996); and Kocienski, Protecting Groups, (Verlag, $3^{rd}$ ed. 2003).

Additionally, the salts of the compounds described herein, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

The term "solvates" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

The compounds, salts and prodrugs described herein can exist in several tautomeric forms, including the enol and imine form, and the keto and enamine form and geometric isomers and mixtures thereof. Tautomers exist as mixtures of a tautomeric set in solution. In solid form, usually one tautomer predominates. Even though one tautomer may be described, the present application includes all tautomers of the present compounds. A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs.

Tautomerizations can be catalyzed by: Base: 1. deprotonation; 2. formation of a delocalized anion (e.g., an enolate); 3. protonation at a different position of the anion; Acid: 1. protonation; 2. formation of a delocalized cation; 3. deprotonation at a different position adjacent to the cation.

The term "analogue" refers to a chemical compound that is structurally similar to another but differs slightly in composition (as in the replacement of one atom by an atom of a different element or in the presence of a particular functional group, or the replacement of one functional group by another functional group). Thus, an analogue is a compound that is similar or comparable in function and appearance, but not in structure or origin to the reference compound.

A "patient," "subject," or "host" to be treated by the subject method may mean either a human or non-human animal, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder.

The terms "prophylactic" or "therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The terms "therapeutic agent", "drug", "medicament" and "bioactive substance" are art-recognized and include molecules and other agents that are biologically, physiologically, or pharmacologically active substances that act locally or systemically in a patient or subject to treat a disease or condition. The terms include without limitation pharmaceutically acceptable salts thereof and prodrugs. Such agents may be acidic, basic, or salts; they may be neutral molecules, polar molecules, or molecular complexes capable of hydrogen bonding; they may be prodrugs in the form of ethers, esters, amides and the like that are biologically activated when administered into a patient or subject.

The phrase "therapeutically effective amount" or "pharmaceutically effective amount" is an art-recognized term. In certain embodiments, the term refers to an amount of a therapeutic agent that produces some desired effect at a reasonable benefit/risk ratio applicable to any medical treatment. In certain embodiments, the term refers to that amount necessary or sufficient to eliminate, reduce or maintain a target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation. In certain embodiments, a therapeutically effective amount of a therapeutic agent for in vivo use will likely depend on a number of factors, including: the rate of release of an agent from a polymer matrix, which will depend in part on the chemical and physical characteristics of the polymer; the identity of the agent; the mode and method of administration; and any other materials incorporated in the polymer matrix in addition to the agent.

With respect to any chemical compounds, the present application is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

When an atom or a chemical moiety is followed by a subscripted numeric range (e.g., $C_{1-6}$), it is meant to encompass each number within the range as well as all intermediate ranges. For example, "$C_{1-6}$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

The term "alkyl" is intended to include both branched (e.g., isopropyl, tert-butyl, isobutyl), straight-chain e.g., methyl, ethyl, propyl, butyl, pentyl, hexyl, heptyl, octyl, nonyl, decyl), and cycloalkyl (e.g., alicyclic) groups (e.g., cyclopropyl, cyclopentyl, cyclohexyl, cycloheptyl, cyclooctyl), alkyl substituted cycloalkyl groups, and cycloalkyl substituted alkyl groups. Such aliphatic hydrocarbon groups have a specified number of carbon atoms. For example, $C_{1-6}$ alkyl is intended to include $C_1$, $C_2$, $C_3$, $C_4$, $C_5$, and $C_6$ alkyl groups. As used herein, "lower alkyl" refers to alkyl groups having from 1 to 6 carbon atoms in the backbone of the carbon chain. "Alkyl" further includes alkyl groups that have oxygen, nitrogen, sulfur or phosphorous atoms replacing one or more hydrocarbon backbone carbon atoms. In certain embodiments, a straight chain or branched chain alkyl has six or fewer carbon atoms in its backbone (e.g., $C_1$-$C_6$ for straight chain, $C_3$-$C_6$ for branched chain), for example four or fewer. Likewise, certain cycloalkyls have from three to eight carbon atoms in their ring structure, such as five or six carbons in the ring structure.

The term "substituted alkyls" refers to alkyl moieties having substituents replacing a hydrogen on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)). If not otherwise indicated, the terms "alkyl" and "lower alkyl" include linear, branched, cyclic, unsubstituted, substituted, and/or heteroatom-containing alkyl or lower alkyl, respectively.

The term "halo" or "halogen" refers to fluoro, chloro, bromo, and iodo. "Counterion" is used to represent a small, negatively charged species such as fluoride, chloride, bromide, iodide, hydroxide, acetate, and sulfate. The term sulfoxide refers to a sulfur attached to 2 different carbon atoms and one oxygen and the S—O bond can be graphically represented with a double bond (S=O), a single bond without charges (S—O) or a single bond with charges [S(+)-O(−)].

The terms "substituted" as in "substituted alkyl," and the like, as alluded to in some of the aforementioned definitions, is meant that in the alkyl, aryl, or other moiety, at least one hydrogen atom bound to a carbon (or other) atom is replaced with one or more non-hydrogen substituents. Examples of such substituents include, without limitation: functional groups such as halo, hydroxyl, silyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO−), carbamoyl (—(CO)—$NH_2$), mono-($C_1$-$C_{24}$ alkyl)-substituted carbamoyl (—(CO)—NH($C_1$-$C_{24}$ alkyl)), di-($C_1$-$C_4$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—$NH_2$), carbamido (—NH—(CO)—$NH_2$), cyano (—CN), isocyano (—N$^+$C$^-$), cyanato (—O—CN), isocyanato (—ON$^+$C$^-$), isothiocyanato (—S—CN), azido (—N=N$^+$=N$^-$), formyl (—(CO)—H), thioformyl (—(CS)—H), amino (—$NH_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, etc.), arylimino (—CR=N(aryl), where R=hydrogen, alkyl, aryl, alkaryl, etc.), nitro (—$NO_2$), nitroso (—NO), sulfo (—$SO_2$—OH), sulfonato (—$SO_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), phosphono (—P(O)(OH)$_2$), phosphonato (—P(O)(O$^-$)$_2$), phosphinato (—P(O)(O$^-$)), phospho (—$PO_2$), and phosphino (—$PH_2$); and the hydrocarbyl moieties $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, and $C_6$-$C_{24}$ aralkyl.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl."

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The terms "free compound" is used herein to describe a compound in the unbound state.

Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

The term "small molecule" is an art-recognized term. In certain embodiments, this term refers to a molecule, which has a molecular weight of less than about 2000 amu, or less than about 1000 amu, and even less than about 500 amu.

All percentages and ratios used herein, unless otherwise indicated, are by weight.

The terms "reducing", "suppressing" and "inhibiting" have their commonly understood meaning of lessening or decreasing.

The term "in vitro" refers to an artificial environment and to processes or reactions that occur within an artificial environment. In vitro environments include, but are not limited to, test tubes and cell culture. The term "in vivo" refers to the natural environment (e.g., an animal or a cell) and to processes or reaction that occur within a natural environment. The term "in silico" refers to a process that is performed on a computer or is simulated on a computer or in virtual reality.

Embodiments described herein relate to compositions and methods of inhibiting carbapenemase or carbapenem-hydrolyzing β-lactamase activity as well as to compositions and methods of treating bacterial infections, such as carbapenem resistant gram negative bacterial infections, in a subject in need thereof. It was found that bisthiazolidines can be used to inhibit and/or inactivate carbapenemase or carbapenem-hydrolyzing β-lactamase activity, and particularly, metallo-β-lactamase enzymatic function. The inhibition of metallo-β-lactamase enzymatic function can occur through a two-step process wherein an initial enzyme (E)-inhibitor (I) complex (EI) undergoes a conformational transition to a more stable species, E*I. The bisthiazolidines also restored the activity of β-lactam antibiotics against β-lactam resistant bacterial infection in whole cell assays. The bisthiazolidines metallo-β-lactamase inhibitors are therefore useful in the treatment of bacterial infections in subjects in need thereof alone or in combination with β-lactam antibiotics and/or with other non-β-lactam antibiotics.

The bisthiazolidine or fused oxazolidine metallo-β-lactamase inihibitor can include at least one compound having the formula:

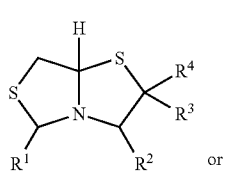

(I)

or

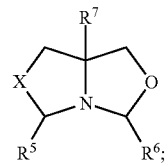

(II)

wherein x is O or S,

R$^1$ is selected from the group consisting of a substituted or unsubstituted $C_1$-$C_{12}$ alkylthio, $C_1$-$C_{12}$ alkyldithio, $C_1$-$C_{12}$ alkylsulfonyl, and $C_1$-$C_{12}$ alkylsulfate, R$^2$ is selected from the group consisting of H, a substituted or unsubstituted carboxy, $C_1$-$C_{12}$ alkyl, $C_1$-$C_{12}$ alkenyl, carboxylato, carbamoyl, $C_1$-$C_{12}$ alcohol, $C_1$-$C_{12}$ alkoxycarbonyl, $C_1$-$C_5$ alkylcarbonato, $C_1$-$C_5$ alkyl-carbamoyl, and hydroxyaminocarbonyl, R$^3$ and R$^4$ are each independently selected from the group consisting of a H, a $C_1$-$C_{12}$ alkyl, and $C_1$-$C_{12}$ alkenyl, and wherein R$^2$ and R$^3$ may be linked to form a cyclic or polycyclic ring, R$^5$ is selected from the group consisting of a substituted or unsubstituted $C_1$-$C_{12}$ alkylthio, $C_1$-$C_{12}$ alkyldithio $C_1$-$C_{12}$ alkylsulfonyl, and $C_1$-$C_{12}$ alkylsulfate, R$^6$ and R$^7$ are each independently selected from the group consisting of H, a substituted or unsubstituted carboxy, $C_1$-$C_{12}$ alkyl, carboxylato, carbamoyl, $C_1$-$C_{12}$ alcohol, $C_1$-$C_{12}$ alkoxycarbonyl, $C_1$-$C_{12}$ alkylcarbonato, $C_1$-$C_{12}$ alkyl-carbamoyl, and hydroxyaminocarbonyl; and pharmaceutically acceptable salts thereof.

In other embodiments, the bisthiazolidine metallo-β-lactamase inihibitor can include at least one compound having the formula:

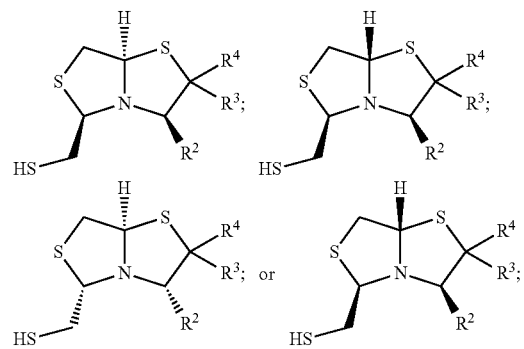

wherein R$^2$ is selected from the group consisting of H, a substituted or unsubstituted carboxy, $C_1$-$C_{12}$ alkyl, $C_1$-$C_{12}$ alkenyl, carboxylato, carbamoyl, $C_1$-$C_{12}$ alcohol, $C_1$-$C_{12}$ alkoxycarbonyl, $C_1$-$C_5$ alkylcarbonato, $C_1$-$C_5$ alkyl-carbamoyl, and hydroxyaminocarbonyl, R$^3$ and R$^4$ are each independently selected from the group consisting of a H, $C_1$-$C_{12}$ alkyl, and $C_1$-$C_{12}$ alkenyl, and wherein R$^2$ and R$^3$ may be linked to form a cyclic or polycyclic ring, and pharmaceutically acceptable salts thereof.

In still other embodiments, the bisthiazolidine metallo-β-lactamase inihibitor can include at least one compound having the formula:

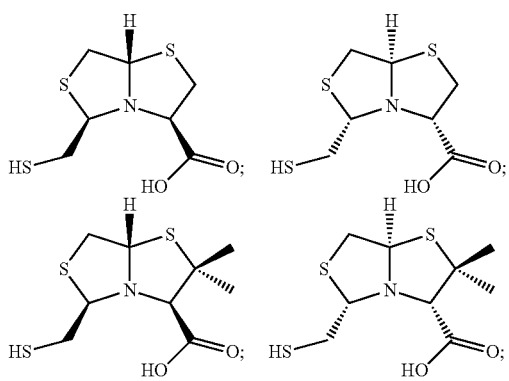

and pharmaceutically acceptable salts thereof.

The bisthiazolidine metallo-β-lactamase inihibitors described herein can be provided in pharmaceutical compositions as an active ingredient in combination with an antibiotic (e.g., a β-lactam antibiotic or some other non β-lactam-lactam antibiotic) and a suitable amount of pharmaceutically acceptable carrier or diluent, so as to provide a form for proper administration to a subject in need thereof. These compositions can be administered by parenteral, in particular intramuscular route, oral, sublingual, rectal, aerosol or by local route in a topical application on the skin and the mucous membranes. Suitable pharmaceutical vehicles include excipients such as starch, glucose, lactose, sucrose, gelatin, gum arabic, malt, rice, flour, chalk, silica gel, sodium stearate, glycerol monostearate, talc, sodium chloride, dried skim milk, glycerol, propylene glycol, water, ethanol, and the like. Other examples of suitable pharmaceutical vehicles have been described in the art. Compositions of the described herein, if desired, can also contain minor amounts of wetting, dispersing or emulsifying agents, or pH buffering agents, and preservatives. In addition, auxiliary, stabilizing, thickening, lubricating, and coloring agents can be included. Pharmaceutical compositions can be formulated in a conventional manner. Proper formulation is dependent upon the route of administration chosen. The present pharmaceutical compositions can take the form of injectable preparations, suspensions, emulsions, sugar-coated tablets, pellets, gelatin-capsules, capsules containing liquids, powders, granules, sustained-release formulations, suppositories, aerosols, sprays, ointments, creams or any other form suitable for use.

In another embodiment, the bisthiazolidine metallo-β-lactamase inihibitors can be used as an active ingredient in an antibacterial composition in admixture with a carrier for the manufacture of a medicament.

In some embodiments, the bisthiazolidine metallo-β-lactamase inihibitors can be used as an active ingredient in an antibacterial composition along with one or more antibiotics (e.g., a β-lactam antibiotic or some other non β-lactam antibiotic), in an antibacterial composition in admixture with a carrier.

The anti-bacterial composition can be formulated for intramuscular, intraperitonial, subcutaneous and intravenous use. Sterile solutions of the active ingredient can be prepared and the pH of the solutions are suitably adjusted and buffered. For intravenous use, the total concentration of solutes should be controlled to render the preparation isotonic. Suitable solvents include saline solution (e.g., 0.9% NaCl solution) and apyrogenic sterile water. Pharmaceutical compositions for oral delivery can be, for example, in the form of tablets, lozenges, aqueous or oily suspensions, granules, powders, emulsions, capsules, syrups, or elixirs. Orally administered compositions can contain one or more optional agents, for example, sweetening agents such as fructose, aspartame, or saccharin, flavoring agents such as peppermint, oil of wintergreen, cherry, coloring agents, and preserving agents to provide a pharmaceutically palatable preparation. Moreover, when in tablet form, the compositions can be coated to delay disintegration and absorption in the gastrointestinal tract, thereby providing a sustained action over an extended period of time. Oral compositions can include standard vehicles such as mannitol, lactose, starch, magnesium stearate, sodium saccharin, cellulose, magnesium carbonate, and the like. For oral liquid preparations, for example, suspensions, elixirs, and solutions, suitable carriers, excipients, or diluents include water, saline, alkyleneglycols (e.g., propylene glycol), polyalkylene glycols (e.g., polyethylene glycol), oils, alcohols, slightly acidic buffers ranging from about pH 4 to about pH 6 (e.g., acetate, citrate, ascorbate ranging from about 5 mM to about 50 mM), and the like. Additionally, flavoring agents, preservatives, coloring agents, bile salts, acylcarnitines, and the like can be added.

For topical formulations of compounds of the present invention, creams, gels, ointments or viscous lotions can be used as appropriate delivery forms. Topical delivery systems also include transdermal patches containing at least one compound of formula (I) to be administered. Delivery through the skin can be achieved by diffusion or by more active energy sources such as iontophoresis or electrotransport. Formulations of a compound of the present invention, for topical use, such as in creams, ointments, and gels, can include an oleaginous or water soluble ointment base, for example, topical compositions can include vegetable oils, animal fats, and in certain embodiments, semisolid hydrocarbons obtained from petroleum. Topical compositions can further include white ointment, yellow ointment, cetyl esters wax, oleic acid, olive oil, paraffin, petrolatum, white petrolatum, spermaceti, starch glycerite, white wax, yellow wax, lanolin, and glyceryl monostearate. Various water-soluble ointment bases can also be used, including glycol ethers and derivatives, polyethylene glycols, polyoxyl 40 stearate, and polysorbates.

In a pharmaceutical composition containing a bisthiazolidine metallo-β-lactamase inihibitor, the weight ratio of active ingredient to carrier will normally be in the range of 1:20 to 20:1. The administered daily dose varies according to the illness treated, and the administration route. However in most instances, an effective dose (e.g., in some instances, a β-lactamase inhibiting dose) of a compound of formula (I) or a pharmaceutically acceptable salt thereof will be a daily dose in the range from about 1 to about 500 mg per kilogram of body weight orally, and from about 1 to about 500 mg per kilogram of body weight parenterally. The weight ratio of the bisthiazolidine metallo-β-lactamase inihibitors and an antibiotic (if it is being administered with an antibiotic, e.g., a β-lactam antibiotic or some other non β-lactam antibiotic) will normally be in the range from 1:20 to 20:1.

In some embodiments, the bisthiazolidine metallo-β-lactamase inihibitors can be used to treat a bacterial infection, prevent a bacterial infection, or reduce the risk of or overcome the development of resistance to an antibiotic. The bisthiazolidine metallo-β-lactamase inihibitors can also be used in an improved method for the treatment of bacterial infections caused by β-lactamase producing bacteria in a subject in need of such treatment. In some embodiments, the bacterial infection can be a β-lactamase producing, carbapenem resistant gram negative bacteria and the bisthiazolidine metallo-β-lactamase inihibitor can be administered to the subject at an amount effective to inhibit carbapenemase or carbapenem-hydrolyzing β-lactamase activity.

In some embodiments, the subject to be treated has one or more symptoms of bacterial infection or is at risk for developing infection, such as a subject that has a viral infection, is undergoing a medical or dental procedure, or whose system has been exposed to one or more conditions conducive to bacterial infection, such as incurring a wound. Urinary tract infections, nosocomial infections including pneumonia, infections associated with medical devices, including catheters, are examples of such infections.

In some cases, the subject has experienced recurrent pathogenic infections. In some cases, the subject has had a bacterial infection diagnosed, whereas in other cases the subject has not yet had a bacterial infection diagnosed. The bacterial infection may be diagnosed by sputum test; blood test, including white blood cell count and/or blood culture; test for antibodies; polymerase chain reaction (including RT-PCR), or a combination thereof, for example. There are published procedures in the art for detection of bacteria comprising a metallo-β-lactamase using microbiology methods with a β-lactam, with and without EDTA, for example. Samples for bacterial analysis may be collected by known methods in the art, including from pus, mucus, sputum, blood, nasal swab, vaginal swab, urine, feces, and so forth, for example.

The subject may be elderly (65 years of age or older) or an infant, in certain embodiments. The subject may or may not have one or more symptoms of a bacterial infection, such symptom(s) including fever, inflammation, heat, swelling, pain, pus production, or a combination thereof, for example. The infection may be in any body part(s), including the blood, lungs, skin, ear, eye, throat, urinary tract, nose, sex organ, stomach, bowel, and so forth.

In some embodiments, the β-lactamase producing gram negative bacteria can be a proteobacteria. Proteobacteria are a major group of gram-negative bacteria, including *Escherichia coli* (*E. coli*), *Salmonella*, *Shigella*, and other Enterobacteriaceae, *Pseudomonas, Moraxella, Helicobacter, Stenotrophomonas, Bdellovibrio*, acetic acid bacteria, *Legionella* etc. Other notable groups of gram-negative bacteria include the cyanobacteria, spirochaetes, green sulfur, and green non-sulfur bacteria. Medically relevant gram-negative cocci include the three organisms that cause a sexually transmitted disease (*Neisseria gonorrhoeae*), a meningitis (*Neisseria meningitidis*), and respiratory symptoms (*Moraxella catarrhalis*). Medically relevant gram-negative bacilli include a multitude of species. Some of them cause primarily respiratory problems (*Hemophilus influenzae, Klebsiella pneumoniae, Legionella pneumophila, Pseudomonas aeruginosa*), primarily urinary problems (*Escherichia coli, Proteus mirabilis, Enterobacter cloacae, Serratia marcescens*), and primarily gastrointestinal problems (*Helicobacter pylori, Salmonella enteritidis, Salmonella typhi*). Gram-negative bacteria associated with hospital-acquired infections include *Acinetobacter baumannii*, which cause bacteremia, secondary meningitis, and ventilator-associated pneumonia in hospital intensive-care units.

In specific embodiments, gram-negative bacteria, such as *Pseudomonas aeruginosa, Pseudomonas putida, Pseudomonas mendocina, Pseudomonas stutzeri, Klebsiella pneumoniae, Klebsiella oxytoca, Proteus mirabilis, Pseudomonas fluorescens, E. coli, Acinetobacter baumanii, Stenotrophomonas maltophilia, Bacteroides fragilis, Serratia marcescens, Klebsiella pneumoniae, Enterobacter aerogenes, Enterobacter cloacae, Shigella flexneri, Aeromonas hydrophila, Aeromonas caviae, Citrobacter freundii, Alcaligenes xylosoxidans*, and/or *Proteus vulgaris* are targeted in the invention, because they are known to contain MBLs.

In some embodiments, the method can include administering to the subject having a bacterial infection caused by β-lactamase producing bacteria a therapeutically effective amount of the bisthiazolidine metallo-β-lactamase inihibitors or a pharmaceutically acceptable salt thereof in combination with a β-lactam antibiotic. In such an embodiment, the compounds can increase the antibacterial effectiveness of β-lactamase susceptible β-lactam, antibiotics, that is, they increase the effectiveness of the antibiotic against infections caused by β-lactamase producing microorganisms in mammalian subjects, particularly in human. In these aspects, this makes the bisthiazolidine metallo-β-lactamase inihibitors valuable for co-administration with β-lactam antibiotics. In the treatment of a bacterial infection, the bisthiazolidine metallo-β-lactamase inihibitors and β-lactam antibiotic can be administered sequentially or simultaneously. When co-administered with a β-lactam antibiotic, the combination of the compound of the invention and the antibiotic can provide an additive or synergistic effect. The term synergystic effect refers to the effect produced when two or more agents are co-administered is greater than the effect produced when the agents are administered individually.

In some aspects, treatment with the bisthiazolidine metallo-β-lactamase inihibitors may precede or follow the treatment with the β-lactam antibiotic, including intervals ranging from minutes to weeks. In some aspects the bisthiazolidine metallo-β-lactamase inihibitors and the β-lactam antibiotic are administered separately (either in separate compositions administered simultaneously or in separate compositions administered at different time intervals), one would generally ensure that a significant period of time did not expire between the times of each delivery, such that the β-lactam antibiotic and the bisthiazolidine metallo-β-lactamase inhibitor would still be able to exert an advantageously combined effect. In such instances, it is contemplated that one would administer both therapeutics within about 1, about 2, about 3, about 4, about 5, about 5, about 6, about 7, about 8, about 9, about 10, about 11, about 12, about 13, about 14, about 15, about 16, about 17, about 18, about 19, about 20, about 21, about 22, about 23, about 24, about 36, about 48, or about 72 hours of each other. In one aspect, both therapeutics are administered within about 6-12 hours of each other. In some situations, it may be desirable to extend the time period for treatment significantly.

The β-lactam antibiotic co-administered with the bisthiazolidine metallo-β-lactamase inhibitor can include a compound with antibiotic property that contains a β-lactam functionality. Examples of β-lactam antibiotics which can be used in combination with the bisthiazolidine metallo-β-lactamase inihibitors are commonly marketed penicillins, cephalosporins, penems, carbapenems and monobactams.

Examples of β-lactam antibiotics which can be used in combination with the bisthiazolidine metallo-β-lactamase inhibitors are commonly used penicillins, such as amoxicillin, ampicillin, azlocillin, mezlocillin, apalcillin, hetacillin, bacampicillin, carbenicillin, sulbenicillin, ticarcillin, piperacillin, methicillin, ciclacillin, talampicillin, oxacillin, cloxacillin, dicloxacillin and commonly used cephalosporins, such as cephalothin, cephaloridine, cefaclor, cefadroxil, cefamandole, cefazolin, cephalexin, cephradine, cephapirin, cefuroxime, cefoxitin, cephacetrile, cefotiam, cefotaxime, cefatriazine, cefsulodin, cefoperazone, ceftizoxime, cefinenoxime, cefinetazole, cephaloglycin, cefonicid, cefodizime, cefpirome, cefepime, ceftazidime, cefpiramide, ceftriaxone, cefbuperazone, cefprozil, cefixime, ceftobiprole, ceftaroline, cefalonium, cefminox, ceforanide, cefuzonam, cefoxitin, cefotetan, loracarbef, cefdinir, cefditoren, cefetamet, cefcapene, cefdaloxime, ceftibuten, cefroxadine, latamoxef (moxalactam), and CXA-101. Carbapenem class of β-lactam antibiotics can include imipenem, meropenem, panipenem, biapenem, doripenem, ertapenem. Monobactam class of β-lactam antibiotics can include aztreonam, carumonam, and tigemonam.

Examples of antibiotics (which are not β-lactam antibiotics) which can be used in combination with the bisthiazolidine metallo-β-lactamase inihibitors include aminoglycosides, quinolones, tetracyclines, glycylcyclines, glycopeptides, lipopeptides, macrolides, ketolides, lincosamides, streptogramin, oxazolidinones, polymyxins, and other compounds known to have antibacterial properties.

Pharmaceutical compositions including the bisthiazolidine metallo-β-lactamase inihibitors and antibiotics can be administered to a subject at a therapeutically effective dosage, e.g., a dosage sufficient to improve the chance of successful prevention or treatment of infection or related disease or disorder. Generally, depending on the intended mode of administration, the pharmaceutically acceptable composition will contain about 0.1% to 100 wt. %, preferably about 0.5% to about 50%, by weight of active compound, the remainder being suitable pharmaceutical excipients, carriers, etc. Actual methods for preparing such dosage forms are known, or will be apparent, to those skilled in this art. For example, see Remington the Science and Practice of Pharmacy, $21^{th}$ ed., Lippincott Williams & Wilkins (2005).

The bisthiazolidine metallo-β-lactamase inihibitors and optionally the antibiotic can be administered prior to a bacterial infection, after infection but prior to the manifestation of symptoms of a disease of disorder associated with the infection, or after the manifestation of symptoms associated with the production of one or more bacterial virulence factors to prevent further bacterial multiplication and to prevent further production of virulence factors thereby hindering development of the disease or its progression.

In another aspect, the bisthiazolidine metallo-β-lactamase inihibitors and β-lactam antibiotics can be used to treat bacteria on or associated with a medical device by contacting the device with the bisthiazolidine metallo-β-lactamase inihibitors and β-lactam antibiotics.

A medical device according to the application can comprise any instrument, implement, machine, contrivance, implant, or other similar or related article, including a component or part, or accessory which is: recognized in the official U.S. National Formulary the U.S. Pharmacopoeia, or any supplement thereof; intended for use in the diagnosis of disease or other conditions, or in the cure, mitigation, treatment, or prevention of disease, in humans or in other animals; or, intended to affect the structure or any function of the body of humans or other animals, and which does not achieve any of its primary intended purposes through chemical action within or on the body of human or other animal, and which is not dependent upon being metabolized for the achievement of any of its primary intended purposes.

A medical device can include, for example, endovascular medical devices, such as intracoronary medical devices. Examples of intracoronary medical devices can include stents, drug delivery catheters, grafts, and drug delivery balloons utilized in the vasculature of a subject. Where the medical device comprises a stent, the stent may include peripheral stents, peripheral coronary stents, degradable coronary stents, non-degradable coronary stents, self-expanding stents, balloon-expanded stents, and esophageal stents. The medical device may also include arterio-venous grafts, by-pass grafts, penile implants, vascular implants and grafts, intravenous catheters, small diameter grafts, artificial lung catheters, electrophysiology catheters, bone pins, suture anchors, blood pressure and stent graft catheters, breast implants, benign prostatic hyperplasia and prostate cancer implants, bone repair/augmentation devices, breast implants, orthopedic joint implants, dental implants, implanted drug infusion tubes, oncological implants, pain management implants, neurological catheters, central venous access catheters, catheter cuff, vascular access catheters, urological catheters/implants, atherectomy catheters, clot extraction catheters, PTA catheters, PTCA catheters, stylets (vascular and non-vascular), drug infusion catheters, angiographic catheters, hemodialysis catheters, neurovascular balloon catheters, thoracic cavity suction drainage catheters, electrophysiology catheters, stroke therapy catheters, abscess drainage catheters, biliary drainage products, dialysis catheters, central venous access catheters, and parental feeding catheters.

The medical device may additionally include either arterial or venous pacemakers, vascular grafts, sphincter devices, urethral devices, bladder devices, renal devices, gastroenteral and anastomotic devices, vertebral disks, hemostatic barriers, clamps, surgical staples/sutures/screws/plates/wires/clips, glucose sensors, blood oxygenator tubing, blood oxygenator membranes, blood bags, birth control/IUDs and associated pregnancy control devices, cartilage repair devices, orthopedic fracture repairs, tissue scaffolds, CSF shunts, dental fracture repair devices, intravitreal drug delivery devices, nerve regeneration conduits, electrostimulation leads, spinal/orthopedic repair devices, wound dressings, embolic protection filters, abdominal aortic aneurysm grafts and devices, neuroaneurysm treatment coils, hemodialysis devices, uterine bleeding patches, anastomotic closures, aneurysm exclusion devices, neuropatches, vena cava filters, urinary dilators, endoscopic surgical and wound drainings, bandages, surgical tissue extractors, transition sheaths and dialators, coronary and peripheral guidewires, circulatory support systems, tympanostomy vent tubes, cerebro-spinal fluid shunts, defibrillator leads, percutaneous closure devices, drainage tubes, bronchial tubes, vascular coils, vascular protection devices, vascular intervention devices including vascular filters and distal support devices and emboli filter/entrapment aids, AV access grafts, surgical tampons, and cardiac valves.

The following examples are included to demonstrate preferred embodiments of the invention. It should be appreciated by those of skill in the art that the techniques disclosed in the examples, which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

We investigated the ability of a set of four bisthiazolidine metallo-β-lactamase inihibitors (BTZs) to inhibit VIM-2 and VIM-24. We assessed the ability of BTZ compounds to act against VIM-2 and studied the effect of the R228L substitution upon inhibitor potency against the clinically significant VIM-24 variant.

Methods

Bacterial strains, cloning and mutagenesis. *P. aeruginosa* PA3 was used to amplify blaVIM-2 with and without the leader sequence (starting at codon 60; position S21). Both products were cloned into the pET-24a(+) vector (Novagen, Darmstadt, Germany) using NdeI and BamHI sites, yielding plasmids pET-24a(+)-bla$_{VIM-2}$ and pET-24a(+)-bla$_{VIM-2-S21}$. Plasmid pET-24a(+)-bla$_{VIM-S-S21}$ was then used as template to obtain plasmid pET-24a(+)-bla$_{VIM-24-S21}$ using the QuickChange XL Site-directed Mutagenesis Kit® (Stratagene). VIM-2 and VIM-24 were expressed in *E. coli* BL21(DE3) pLys cells (LifeTechnologies).

A forward primer containing the SacI restriction site and a reverse primer with the BamHI restriction site were used to amplify bla$_{VIM-2}$ including the pET24a(+) ribosomal binding site, using plasmid pET-24a(+)-bla$_{VIM-2}$ as template. The product was then subcloned into phagemid pBCSK (−) (Agilent (Santa Clara, Calif.)) using the above restriction sites, and thus placing the bla$_{VIM-2}$ open reading frame under control of the lac promoter, to yield phagemid pBCSK (−) bla$_{VIM-2}$.

*E. coli* DH10B (Invitrogen, Carlsbad, Calif.) was used as a host strain for pBCSK (−) bla$_{VIM-2}$, and to obtain a mutant library at position 228 by site-saturation mutagenesis, using the QuickChange XL Site-directed Mutagenesis Kit (Stratagene). Briefly, primers that capture all 19 variants at MBL position 228 were designed and PCR mutagenic reactions were conducted using pBCSK (−) bla$_{VIM-2}$ as a template, and transformed into *E. coli* DH10B. Single colonies were selected for plasmid purification, and successful mutagenesis was verified by complete DNA sequencing.

Cell-based Assays

In order to test the phenotypic effect of amino acid substitution, the minimum inhibitory concentrations (MICs) of ampicillin, cephalothin, ceftriaxone, ceftazidime, cefotaxime, cefepime, imipenem, and aztreonam, were determined for each clone in the variant library by the agar dilution method using cation-adjusted Mueller-Hinton agar (MHA), following Clinical and Laboratory Standards Institute recommendations. Ampicillin, cefotaxime, and cephalothin were purchased from Sigma (St. Louis, Mo.), and imipenem was purchased from U.S. Pharmacopeia (Rockville, Md.). The effect of $Zn^{2+}$ availability was also tested by agar dilution using MH supplemented with 250 μM ZnSO4 or 5 μM EDTA. Reported values are the mode of at least 3 biological replicates.

In Vitro Time-kill Study

VIM-2 producing *P. aeruginosa* (imipenem MIC=32 mg/L) and VIM-24 producing *K. pneumoniae* (imipenem MIC=2 mg/L) were cultured overnight at 37° C. in Muller Hinton Broth (MHB) supplemented with 50 mg/L ampicillin. The following day, 1.5 μl of the overnight cultures were inoculated in a 1 ml MHB to obtain a bacterial suspension of approximately $10^6$ CFU/ml.

In order to examine the effects of the BTZ compounds on bacterial growth, the bacterial suspensions were grown at 37° C. under different conditions: MHB alone (growth control), or supplemented with 0.4% DMSO (growth control), sub-lethal concentrations of imipenem (8 mg/L for the *P. aeruginosa* and 0.5 mg/L for the *K. pneumoniae*), 100 mg/L of each inhibitor, or a combination of imipenem and each inhibitor. Samples (10 μl) were removed at time intervals of 100, 300 and 500 min of exposure, and serial dilutions were performed on MHB. The number of viable cells was determined by spotting 20 μl of each dilution on MHA. The plates were incubated at 37° C. overnight, and the numbers of colonies were counted. Results shown are the mean of three biological replicates.

Statistical analysis was performed using R Version 3.1.1. Additional R packages lme4 and multcomp were utilized. A linear mixed-effects model was estimated to address the repeated measures performed within sample. Within each level of time, post-hoc pairwise tests were performed comparing Imipenem to other conditions. This yielded a total of twelve pairwise tests per experiment. These p-values were Bonferroni-adjusted.

Immunoblotting

*E. coli* DH10B cells carrying pBC SK (−) blaVIM-R228X plasmids were grown in LB broth with 20 mg/L chloramphenicol to mid-log phase (OD$_{600nm}$=0.7-0.8). Immunoblotting was performed as described previously (29), with two changes explained as follows. Firstly, 1 ml of cells were pelleted, the supernatant removed, and the pellet frozen at −20° C. overnight. Next, pellets were resuspended in 50 μl of buffer lysis containing 50 mM Tris-HCl pH 7.4, 0.04 mg/ml lysozyme, 1 mM MgSO4, and 5 U/ml benzonuclease (Novagen; Darmstadt, Germany). After 30 min of incubation at 25° C. the solution was spun at 10,000×g and 10 μl of the supernatant were loaded into each lane of a sodium dodecyl sulfate polyacrylamide gel electrophoresis (SDSPAGE) gel. Secondly, a 1:20,000 dilution of anti-DNAK rabbit monoclonal antibody was added as a loading control (Enzo Life Sciences, Farmingdale, N.Y.).

Protein Purification

*E. coli* BL21(DE3) pLys cells carrying pET-24a(+)-bla-VIM-2-S21 or bla$_{VIM-24-S21}$ phagemids were grown in LB containing 50 mg/L kanamycin for 18 hrs. Subsequently cells expressing the plasmid were grown in super optimal broth (SOB) with constant shaking at 200 rpm, until OD$_{600\ nm}$=0.6, then 2 mM ZnSO4 and 0.1 mM isopropyl-β-Dthiogalactopyranoside (IPTG) was added for induction and the cells were incubated for additional 20 h at 20° C. with constant shaking at 200 rpm. Cells were harvested and frozen for 18 h at −20° C. Pellets were resuspended in 50 mM Tris-Cl pH 7.4, containing 200 mM NaCl and 2 mM ZnSO$_4$, lysed with 40 mg/L lysozyme, and 1.0 U/ml benzonase nuclease (Novagen; Darmstadt, Germany). Cells were further lysed using the Sonic Dismembrator Model 500 (3 pulses of 30 sec at 50% amplitude; Fisher Scientific, Waltham, Mass.) and then centrifuged at 12,000 rpm for 10 min to remove the cellular debris.

After an overnight dialysis against 50 mM Tris-Cl pH 7.4, containing 2 mM ZnSO$_4$, VIM-2 and VIM-24 were purified by anion-exchange chromatography (Q HiTrap Sepharose Fast Flow or Source 15Q; GE Healthcare) followed by gel filtration (Superdex 75 10/300 GL, GE Health-care). Enzymes were stored at 4° C. in 50 mM Tris HCl with 2 mM ZnSO$_4$ (pH 7.4). Purity was assessed by SDS-PAGE with final acrylamide concentrations of 12% and 5% (wt/vol) for the resolving and the stacking gels, respectively; Coomasie Blue staining was used for protein band visualization. Once 95% purity was achieved, the $Zn^{2+}$ content was measured using the colorimetric reagent 4-(2-pyridylazo) resorcinol (PAR) under denaturing conditions.

For X-ray crystallography, VIM-2 was expressed and purified as previously described and concentrated by centrifugal ultrafiltration to a final concentration of 15 mg/ml.

Electrospray Ionization (ESI) Mass Spectrometry (MS)

To confirm the molecular weight of the purified VIM-2 and VIM-24 MBLs, ESI-MS was performed on a Waters SynaptG2-Si quadrupole-time-of-flight (Q-TOF) mass spectrometer equipped with a LockSpray dual electrospray ion source, using glu-1-fibrinopeptide B as the lock mass. The Synapt G2-Si was calibrated with sodium iodide using a 50-2000 m/z mass range. For the experiments performed herein, samples were desalted and concentrated using a C18 ZipTip (Millipore, Billerica, Mass.) according to the manufacturer's protocol. Eluted protein samples were diluted with 50% acetonitrile and 0.2% formic acid and directly infused at a rate of 50 µL per mM, and data were collected for 1 mM Lock mass spectra were collected prior to each sample in a similar manner. The tune settings for each data run were as follows: capillary voltage at 3.2 kV, sampling cone at 30, source offset at 30, source temperature at 100° C., desolvation temperature at 450° C., cone gas at 50 L/h, desolvation gas at 600 L/h, and nebulizer bar at 6.0. Spectra were analyzed using MassLynx v4.1. Spectra were modified for lock mass deviations by applying a gain factor and deconvoluted using the MaxEnt 1 program.

Circular Dichroism (CD) Spectroscopy and Thermal Denaturation Analyses

CD experiments were performed in a Jasco (Easton, Md.) J-815 spectrometer with a Peltier effect temperature controller. Quartz cells with a 0.1-cm path length were used for all experiments. For CD spectra, 10 µM VIM-2 or VIM-24 were incubated alone in 10 mM HEPES (pH 7.5) containing 0.2 M NaCl. CD spectra were obtained at 20° C., and data points were recorded every 0.1 nm between λ200 and λ260 with a scan rate of 20 nm/min. For thermal denaturation, 10 µM VIM-2 or VIM-24 were monitored for helical content by CD at λ222 between 20° C. and 85° C. with a heating rate of 2° C./min Data were fit to a two-state model as previously described.

Molecular Modeling

The crystal structure coordinates of VIM-2 (PDB entry 2YZ3) were used to construct a model of the VIM-24 enzyme using Discovery Studio 3.1 (DS 3.1; Accelrys, Inc., San Diego, Calif.). The crystallographic waters were taken out and the enzyme structure was immersed in a water box (7 Å from any face of the box) using explicit periodic boundary conditions (PBC). VIM-24 model was created using Build module of DS by mutation at position 228 from Arginine to Leucine.

The molecule was prepared for energy minimization adding hydrogen and setting the pH of 7.4. The system was minimized in several steps, with Steepest Descendent and Conjugate Gradient algorithms to reach the minimum convergence (i.e., 0.01 after 10,000 iterations). All energy minimizations were carried out using CHARMm force-field parameters. The Particle Mesh Ewald (PME) method was used to treat long-range electrostatic interactions. Bonds that involved hydrogen atoms were constrained with SHAKE algorithm.

To model the complex with VIM-24, co-ordinates and restraints for unhydrolyzed cefepime were generated using JLigand and docked manually into the VIM-24 structure (generated as described above) using Coot. Docking was based upon the assumptions of interactions between the oxygen of the C8 carbonyl with Zn1 and the C3 carboxylate with Zn2, as previously proposed for binding of intact β-lactams to binuclear MBLs. Comparisons with the structure of NDM-1 bound to hydrolyzed meropenem (PDB ID 4EYL) were useful in positioning the molecule relative to the metal ions. The resulting complex structure was minimized using the Yasara server (http://www.yasara.org/minimizationserver.htm). For comparison with VIM-2, the complex was superposed onto the crystal structure of the native enzyme (PDB ID 1KO3) using SSMSuperpose.

Determination of Steady-state Kinetic Parameters

Steady-state reactions were followed using an Agilent (Santa Clara, Calif.) 8453 Diode Array spectrophotometer as previously described. Briefly, each assay was performed in 10 mM HEPES at pH 7.5 supplemented with 200 mM NaCl, 50 µM Zn2SO$_4$ and 50 µg/ml bovine serum albumin (BSA) at 25° C. using nitrocefin (NCF), ampicillin, cephalothin, ceftazidime, cefepime, and imipenem as substrates at an excess molar concentration to establish pseudo-first-order kinetics. Excess metal is required in the buffer to maintain the concentration of active enzyme constant, and hence to assure steady-state conditions, as there is metal dissociation during turnover. The following extinction coefficients were used: NCF, $\Delta_{\epsilon 482}$=17,400 M$^{-1}$ cm$^{-1}$; ampicillin, $\Delta_{\epsilon 235}$=900 M$^{-1}$ cm$^{-1}$; cephalothin, $\Delta_{\epsilon 262}$=7660 M$^{-1}$ cm$^{-1}$; ceftazidime, $\Delta_{\epsilon 256}$=7600 M$^{-1}$ cm$^{-1}$; cefepime, $\Delta_{\epsilon 260}$=750 M$^{-1}$ cm$^{-1}$; and imipenem, $\Delta\Sigma 299$=-9000 M$^{-1}$ cm$^{-1}$. For velocity determinations for ampicillin, cephalothin, NCF, and imipenem, a 1-cm path length quartz cuvette was employed. For ceftazidime and cefepime, a 0.2-cm path length quartz cuvette was used. A nonlinear leastsquares fit of the data (Henri Michaelis-Menten equation) using Enzfitter (Biosoft Corporation, Ferguson, Mo.) was employed to obtain the steady-state kinetic parameters V$_{max}$ and K$_M$ according to equation 1.

$$v = \frac{k_{cat}*[S][E]}{k_m + [S]} \quad (1)$$

In order to estimate the k$_{cat}$ values from the V$_{max}$ obtained from the fits, the Zn$^{2+}$ content of each protein preparation was taken into account to calculate the concentration of active enzyme, as a small fraction of the MBL is found in an irreversibly inactive apo form, which remains inactive even in the presence of excess metal. In the case of cefepime and ceftazidime, where velocities of hydrolysis did not reach saturation under the conditions tested, the k$_{cat}$/KM ratio was calculated by fitting hydrolysis curves to equation 2, $$A_t = A_f + (A_0 - A_f)e^{-kt} \quad (2)$$

where At is absorbance at time t, and Af and Ao represent the final and initial absorbance, respectively. In this equation the observed first-order rate constant k=k$_{cat}$/K$_M$*[E].

Additionally, cefepime and ceftazidime hydrolysis were measured using periplasm preparations, as previously described. Briefly, periplasmic preparations of E. coli DH10B pBC SK (−) harboring bla$_{VIM-2}$ or bla$_{VIM-24}$ were obtained by osmotic shock with chloroform, and MBL production assessed by immunoblotting. Initial velocities of hydrolysis at high substrate concentrations (800 µM for cefepime and 400 µM for ceftazidime) were measured using equal amounts of both β-lactamases in 15 mM HEPES pH 7.5, 200 mM NaCl, supplemented with 50 µM ZnSO$_4$, at 25° C.

Analysis of BTZ inhibition kinetics. Models involving one, or two-step slow binding were considered to analyze BTZ inhibition of NFC hydrolysis by VIM-2 and VIM-24 (Scheme 1).

$$E + I \underset{K_{-1}}{\overset{K_1}{\rightleftarrows}} EI \underset{K_{-2}}{\overset{K_2}{\rightleftarrows}} E*I \quad \text{(Scheme 1)}$$

Here E represents the free enzyme, and I the free inhibitor, EI is the final enzyme-inhibitor complex for a single step slow binding mechanism, and E*I is the enzyme-inhibitor complex formed after conformational changes in a two-step slow binding mechanism. Therefore, the dissociation constant for the EI complex ($K_i$), also called the inhibitor constant, is defined as $K_i = k_{-1}/k_1$; the dissociation constant for the E*I complex ($K_i'$) is defined as $K_i' = k_{-2}/k_2$, and the overall dissociation constant for the two-step mechanism ($K_i^*$) is defined as $K_i^* = K_i/(1+(k_2/k_2))$.

The $K_i$ for each inhibitor was determined by direct competition assays under steady-state conditions. The initial velocity was measured in the presence of a constant concentration of enzyme (3 nM for VIM-2 and 4 nM for VIM-24) with increasing concentrations of inhibitor (5-60 µM) against a fixed concentration (5 x KM) of the indicator substrate, NCF, as previously described (42-44). The reactions were started by addition of VIM-2 or VIM-24 to substrate or to mixtures of substrate and inhibitor. Data were linearized by plotting inverse initial steady-state velocities (1/v0) against inhibitor concentration (I). $K_i$ (observed) was determined by dividing the value for the y intercept by the slope of the line. $K_i$ determinations were corrected to account for the affinity of NCF for the β-lactamase according to equation 3.

$$k_i = \frac{k_{i(obs)}}{\left[1 + \left(\frac{[S]}{k_{MNFC}}\right)\right]} \quad (3)$$

Measurements of association rate constants for inhibitor binding were carried out at 25° C. in 10 mM HEPES at pH 7.5 supplemented with 200 mM NaCl, 50 µM Zn2SO4 and 50 µg/ml BSA, in the presence of several concentrations of each compound. Reactions were then initiated by the addition of β-lactamase (3 nM VIM-2 or 4 nM VIM-24) to a mixture of 50 µM NCF and each BTZ without pre-incubation. Inhibitor association rate constants were estimated from linear extrapolation of the observed rate constant for inhibition (kobs), which was obtained by fitting progress curves of NFC hydrolysis to Eq. 4:

$$A = A_0 + v_s t + \frac{(v_0 - v_s)(1 - e^{-k_{obs}t})}{k_{obs}} \quad (4)$$

where A is absorbance, $v_0$ is the initial and $v_s$ the steady-state velocity of the reaction, and $k_{obs}$ is the apparent rate constant for formation of the enzyme-inhibitor complex.

As previously described, the linear dependence of $k_{obs}$ vs. [I] at limiting I concentration approximates second-order rate constant $k_2/K_i$. The observed second-order rate constant also includes an adjustment for competition between inhibitor and substrate binding (Eq. 5).

$$k_{obs} = k_{-2} + \frac{k_2}{k_i} \frac{[I]}{\left(1 + \frac{[S]}{km}\right)} \quad (5)$$

Also, $v_s$ calculated from the progress curves of NCF hydrolysis for each concentration of inhibitor were used to determine $K_i^*$, according to the relationship shown in equation 6 (5). The value reported is the mean of three velocities±SD.

$$v_s = \frac{V_{max} * S}{S + Km\left(1 + \frac{I}{K_i^*}\right)} \quad (6)$$

To further test the time-dependent inhibition mechanism of inhibitor binding, assays using dilutions of pre-formed complexes were performed. For these experiments, 1 µM of enzyme was incubated with varying concentrations of the inhibitor which allowed for complete inactivation of the enzyme during the 5 min incubation at 25° C. The reactions were then diluted 2,000-fold in 10 mM HEPES at pH 7.5 supplemented with 200 mM NaCl, 50 µM Zn2SO4 and 50 µg/ml BSA, which contained 50 µM NCF. Reactivation of the enzyme based on NCF hydrolysis was monitored over time. Control reaction with the free enzyme was performed in the same fashion.

Crystallization, Data Collection and Structure Determination

Conditions for cocrystallization were identified by using a mixture of VIM-2, purified as described previously, and the BTZ compound L-CS319 (dissolved in dimethyl sulfoxide and added to the protein sample to a final concentration of 10 mM) in sparse-matrix crystallization screening experiments. The final DMSO concentration was maintained at 10% v/v or less. Diffraction quality crystals were obtained from 0.1 M Bicine pH 9.0; 65% 2-methyl-2,4-pentandiol. Crystals were mounted in rayon loops and snap-frozen in liquid nitrogen prior to data collection. Diffraction data were collected on beam line I04-1 of the Diamond Light Source synchrotron (Didcot, U.K.) using a Pilatus detector. Images were integrated, scaled and merged using the programs XDS, POINTLESS and SCALA as implemented in the XIA2 crystallography pipeline. The structure was solved by molecular replacement with PHASER using the native (unliganded) VIM-2 structure as a search model (PDB ID 1KO3;) and subjected to alternate rounds of model-building and refinement using Coot and Refmac5 as implemented in the CCP4 crystallography suite. The quality of the final model was assessed using the MolProbity server. Co-ordinates and structure factors have been deposited in the protein data bank with accession number 4UA4.

Synthesis of Bisthiazolidines 1f-j

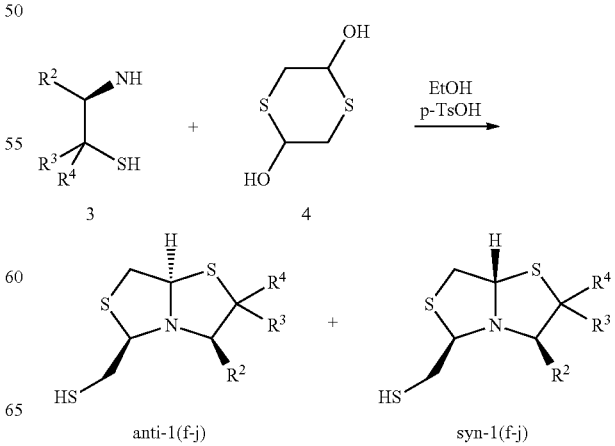

-continued

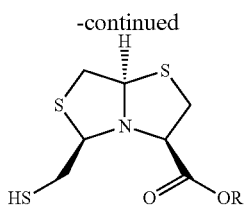

1f R = H
1g R = OEt

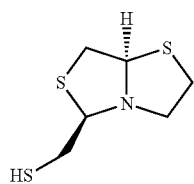

1h

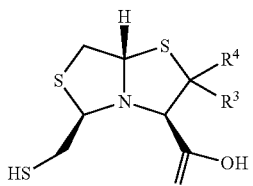

1i

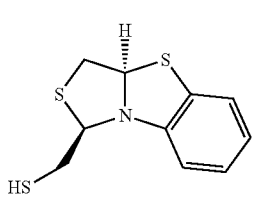

1j (2R,3S,8R)-8-carboxylate-2-mercaptomethyl-1-aza-3,6-dithiobicyclo[3.3.0]octane (trans-1 f)

To a stirred suspension of 1-cysteine (0.5 g, 4.1 mmol) in EtOH (16 mL), was added 1,4-dithiane-2,5-dithiol 4 (0.8 g, 5.0 mmol) and p-TsOH ac (0.030 g, 0.17 mmol). The mixture was heated to reflux for 2 h. Then it was cooled down and poured into brine, extracted with CH2Cl2 (5×30 mL), dried (Na2SO4) and filtered. The solvent was removed under reduced pressure and the residue was purified by chromatography on SiO2 (EtOAc/hexanes/AcOH, 1:3:0.1) to led compound 1f (0.830 g, 86%, trans/cis 95/05) as a white solid:mp 103-104° C.; $^1$H NMR (CDCl3) δ 1.86 (t, J=8.5 Hz, $^1$HSH), 2.81 (dd, J=8.5, 6.9 Hz, 2H), 3.11 (dd, J=12.0, 4.2 Hz, $^1$H), 3.33 (dd, J=11.4, 7.1 Hz, $^1$H), 3.43 (dd, J=11.4, 3.3 Hz, $^1$H), 3.55 (dd, J=12.0, 5.8 Hz, $^1$H), 4.25 (dd, J=7.1, 3.3 Hz, $^1$H), 4.32 (t, J=6.9 Hz, $^1$H), 5.05 (dd, J=5.8, 4.2 Hz, $^1$H), $^{13}$C NMR ((CD3)2CO) δ 34.0, 34.3, 39.2, 71.5, 74.5, 75.6, 172.1; HRMS calculated for C7H11NO2S3, [M+H]+238.0025, found: 238.0033; αD=−57.7° (20° C., AcCN, c=0.6).

(3S,5R,7aR)-ethyl 5-(thiomethyl)tetrahydro-2H-thiazolo[4,3-b]thiazole-3-carboxylate (trans-1g)

Prepared in analogous route as described for trans-1f, starting from 1-cysteine ethyl ester HCl. Purification by chromatography on SiO2 (1:3, EtOAc:hexanes) led to compound 1g (89%, trans/cis 95/05) as an oil: trans-1g: $^1$H NMR (CDCl3) δ 1.30 (t/=7.1 Hz, 3H), 1.98 (dd, J=9.5, 7.5 Hz, $^1$H), 2.64 (ddd, J=13.6, 9.5, 6.1 Hz, $^1$H), 2.89 (dd, J=13.6, 7.5, 7.5 Hz, $^1$H), 3.09 (dd, J=11.8, 3.9 Hz, $^1$H), 3.28 (dd, 0.1=10.9, 6.6 Hz, $^1$H), 3.32 (dd, J=10.9, 5.1 Hz, $^1$H), 3.54 (dd, J=11.8, 5.5 Hz, $^1$H), 4.21 (dd, J=6.6, 5.1 Hz, $^1$H), 4.23 (q, J=7.1 Hz, 2H), 4.30 (dd, J=7.5, 6.1 Hz, $^1$H), 5.09 (dd, J=5.3, 3.9 Hz, H); $^{13}$C NMR (CDCl3) δ 14.1, 33.7, 34.2, 39.1, 61.7, 70.3, 73.3, 74.9, 170.4; HRMS calculated for C9H16NO2S3, [M+H]+266.0343, found 266.0329; [α]D=−256° (20° C., MeOH, c=0.6).

±(5RS,7aRS)-tetrahydro-2H-thiazolo[4,3-b]thiazol-5-yl)methanethiol (trans-1h)

Prepared in an analogous route as described for trans-1f, starting from cysteamine Purification by chromatography on SiO2 (1:6, EtOAc:hexanes) led to compound 1h (68%, trans/cis 92:08) as an oil: $^1$H NMR (CDCl3) δ 1.84 (dd, J=9.1, 7.6 Hz, $^1$H), 2.65 (ddd, J=13.6, 9.1, 6.0 Hz, $^1$H), 2.82 (ddd, J=13.6, 7.6, 7.0 Hz, $^1$H), 3.12 (m, $^1$H), 3.08 (m, 2H), 3.21 (ddd, J=11.5, 7.2, 6.6 Hz, $^1$H), 3.48 (ddd, J=11.5, 5.7, 4.8 Hz, $^1$H), 3.54 (ddd, J=11.6, 5.2, 0.5 Hz, $^1$H), 4.24 (dd, J=7.0, 6.0 Hz, $^1$H), 4.97 (dd, J=5.2, 3.7 Hz, $^1$H); $^{13}$C NMR (CDCl3) δ 31.8, 33.5, 38.4, 57.1, 73.2, 74.5; HRMS calculated for C6H12NS3, [M]+194.0132, found: 194.0156.

2R,5S,8R)-2-mercaptomethyl-dimethyl-8-carboxylate-1-aza-3, 6-dithiobicyclo[3.3.0]octane cis-1-1i)

Prepared in analogous route as described for 1f, starting from 1-penicillamine. Purification by chromatography on SiO2 (1:3, EtOAc:hexanes) led to compound 1i (89%, cis/trans: 95:05).

Cis-1-1i white solid, mp 89-97° C.; $^1$H NMR (CDCl3) δ 1.52 (s, 3H), 1.62 (s, 3H), 1.89 (t, 0.1=8.71 Hz, 1HSH), 2.81 (m, 2H), 3.06 (dd, J=11.7, 5.4 Hz, $^1$H), 3.43 (dd, J=11.7, 6.6 Hz, 1H), 3.80 (s, 1H), 4.31 (t, J=7.3 Hz, 1H), 4.98 (dd, J=6.6, 5.41 Hz, $^1$H); 13CNMR(CDCl3) δ 28.0, 28.1, 32.0, 40.5, 55.1, 68.7, 75.7, 78.5, 170.4; HRMS calculated for C9H16NO2S3, [M+H]+266.0343, found 266.0330; [α]D=45.2° (20° C., MeOH, c=1.0).

Trans-1-1i foamy oil, $^1$H NMR (CDCl3) δ 1.49 (s, 3H), 1.66 (dd, J=9.0, 8.3 Hz, 1HSH), 1.77 (s, 3H), 2.66 (m, 1H), 2.87 (m, 1H), 3.21 (dd, J=10.1, 5.2 Hz, $^1$H), 3.38 (dd, J=10.1, 8.1 Hz, 1H), 3.97 (s, $^1$H), 4.55 (dd, J=7.3, 5.7 Hz, 1H), 5.07 (dd, 0.1=8.1, 5.2 Hz, 1H); 13CNMR(CDCl3) δ 25.6, 32.9, 33.9, 40.5, 58.6, 70:1, 70.5, 77.0, 174.6.

(2S,5R,8S)-2-mercaptomethyl-7-dimethyl-8-carboxylate-1-aza-3,6-dithiobicyclo[3.3.0]octane cis-D-1i Prepared in an analogous route as described for 1f, starting from d-penicillamine. The residue was purified by chromatography on SiO2 (1:3, EtOAc:hexanes led to compound cis-d-1j (76%, trans/cis: 01:99). The spectroscopic properties were identical to those obtained for cis-L-1i, [α]D=40.0° (20° C., MeOH, c=1.0).

±(2RS,5RS) 1-thiomethyl-3,3a-dihydro-benzo[d]thiazolo[4,3-b]thiazole (trans-1j)

Prepared in an analogous route as described for trans-1f, starting from o-amino-mercaptobenzene, the residue was purified by chromatography on SiO2 (1:3, EtOAc:hexanes) led to compound 1j (96%, trans/cis: 99:01) as an oil; $^1$H NMR (CDCl3) δ 1.91 (dd, 0.1=10.8, 6.3 Hz, $^1$H), 2.72 (ddd, 0.1=13.8, 10.8, 4.8 Hz, $^1$H), 2.93 (dd, J=11.8, 8.7 Hz, $^1$H), 2.99 (ddd, J=13.8, 9.0, 6.3 Hz, $^1$H), 3.23 (dd, J=11.8, 5.3 Hz, 1H), 5.11 (dd, J=8.7, 5.3 Hz, $^1$H), 5.19 (dd, J=9.0, 4.8 Hz, $^1$H), 6.88 (m, 2H), 7.11 (m, 2H); $^{13}$CNMR(CDCl3) δ 33.5, 40.0, 70.2, 70.5, 110.9, 122.2, 123.0, 124.5, 126.2, 145.2; HRMS calculated for C10H12NS3 [M+H]+242.0132, found 242.0119.

Results

Effects of the R228 Substitution on the Phenotype and Expression of VIM-2 Variants Expressed in *E. coli*

To determine the effect of the R228L substitution and to investigate the role of position 228 in VIM MBLs, we generated all possible variants at this position by site-saturation mutagenesis, and assessed the impact of these substitutions on phenotype by antibiotic susceptibility testing against a variety of β-lactams (Table 1). Compared to VIM-2, the natural R228L substitution in VIM-24 increased resistance to cefepime (≤0.5 mg/L vs. 4 mg/L) and ceftazidime (16 mg/L vs. 64 mg/L), while the minimal inhibitory concentration (MIC) values for all the remaining antibiotics tested remained relatively unchanged. Results from the R228X library also showed this position to be tolerant of substitution as only two variants, R228K and R228P, displayed significant reductions in MIC, compared to VIM-2, for all the antibiotics tested. Remarkably, R228M and R228Q showed increased resistance towards all β-lactams, including imipenem, and thus represented "gain of function" mutations.

An additional factor that can affect antibiotic resistance is the expression level of the individual VIM variants. Therefore, we next evaluated the steady-state expression of each of the variants expressed from pBCSK (−) in *E. coli* DH10B cells, by immunoblotting. The results on whole cell extracts showed all variants to be produced at either the same level of the wild type VIM-2 or lower (FIG. 3A). For instance, the R228K and R228Q variants are expressed at a level comparable to the wild type, whereas the expression of the R228M variant is lower. We assert that phenotypic differences arise from a combination of inherent properties (sequence and/or structure stability) that affects catalytic activity. The deficient resistance conferred by the R228K enzyme may then be explained by structural changes that disrupt the conformation of the active site loop 10 (ASL-10) and may also indirectly reduce the affinity for $Zn^{2+}$. In the case of the "gain of function" variants, R228M and R228Q, despite the absence of a strongly charged side chain at position 228, both the Met and Gln substitutions clearly retain the ability to bind substrate in a productive orientation for hydrolysis. These data imply that, in the absence of a significant stabilizing interaction with the R228 side chain, the C3 or C4 carboxylate of the substrate can make alternative contacts with the enzyme active site that are still compatible with efficient hydrolysis. More detailed studies of the R228Q, R228M and R228K variants will thus provide

TABLE 1

Cell-based assays using *E. coli* DH10B pBCSK(−), producing VIM-2, VIM-24 (R228L), and other variants

|  | E. coli pBC SK(−) | VIM-2 (228R) | VIM-24 (R228L) | R228K | R228P | R228M | R228Q | R228Y | R228X[c] |
|---|---|---|---|---|---|---|---|---|---|
| Ampicillin | 4 | 512 | 512 | 32 | 32 | 1024 | 1024 | 1024 | 512-64 |
| Cephalothin | 8 | 256 | 256 | 16 | 16 | 256 | 1024 | 256 | 256-64 |
| Ceftriaxone | 0.5 | 8 | 8 | 1 | 0.5 | 16 | 32 | 16 | 16-1 |
| Cefotaxime | 0.06 | 8 | 16 | 1 | 1 | 16 | 32 | 16 | 32-2 |
| Aztreonam | ≤0.125 | ≤0.125 | ≤0.125 | ≤0.125 | ≤0.125 | ≤0.125 | ≤0.125 | ≤0.125 | ≤0.125 |
| Ceftazidime | 0.06 | 16 | 64 | 1 | 1 | 128 | 128 | 64 | 128-16 |
| Ceftazidime + Zn[a] | ≤1 | 32 | 128 | ≤1 | 4 | 256 | 512 | 128 | 256-32 |
| Ceftazidime + EDTA[b] | ≤1 | 16 | 32 | ≤1 | ≤1 | 64 | 128 | 64 | 64-8 |
| Cefepime | 0.03 | 0.5 | 4 | 0.5 | 0.25 | 2 | 16 | 8 | 4-1 |
| Cefepime + Zn[a] | ≤0.25 | 0.5 | 4 | ≤0.25 | 0.5 | 2 | 32 | 8 | 4-1 |
| Cefepime + EDTA[b] | ≤0.25 | 0.5 | 4 | ≤0.25 | ≤0.25 | 4 | 16 | 8 | 2-1 |
| Imipenem | 0.25 | 0.5 | 0.5 | 0.25 | 0.5 | 2 | 4 | 1 | 1-0.25 |
| Imipenem + Zn[a] | 0.25 | 1 | 1 | 0.25 | 0.25 | 4 | >4 | 1 | 2-0.5 |
| Imipenem + EDTA[b] | ≤0.125 | 0.5 | 0.5 | 0.25 | ≤0.125 | 1 | 4 | 1 | 1-0.25 |

[a]MHA supplemented with a final concentration of 250 μM $Zn^{2+}$,
[b]MHA supplemented with 5 μM EDTA,
[c]Values shown in this column are the ranges of the MIC values obtained for the other variants. A complete list of the MICs is provided as supplemental information MBLs are exported to the bacterial periplasm as unfolded polypeptides, and metal incorporation takes place in the periplasmic space where $Zn^{2+}$ availability is limited. Thus, MBLs with reduced capability to bind $Zn^{2+}$ are deficient in conferring resistance. Accordingly, we determined the MIC values of our R228X library in *E. coli* cells in media containing excess or limiting concentrations of $Zn^{2+}$ using cefepime, ceftazidime and imipenem as representative antibiotics. As shown in Table 1, the effect of $Zn^{2+}$ availability on resistance was especially noticeable for ceftazidime, for which VIM-24, but also 90% of the in vitro generated variants, displayed higher MICs. Increments of up to 2 doubling dilutions (MIC increases from 128 to 512 mg/L) were detected in conditions of high $Zn^{2+}$ availability. Of note, consistent decreases in resistance, especially in restricted $Zn^{2+}$ media, were observed for only two variants, R228P and R228K. Furthermore, the activity of the R228K variant was not improved in Zn2+ supplemented agar.

insights into the basis of substrate specificity, and the catalytic mechanism, of VIM enzymes.

Consequences of R228L Substitution for VIM-2 Structure and Catalytic Activity

Figure 3E:
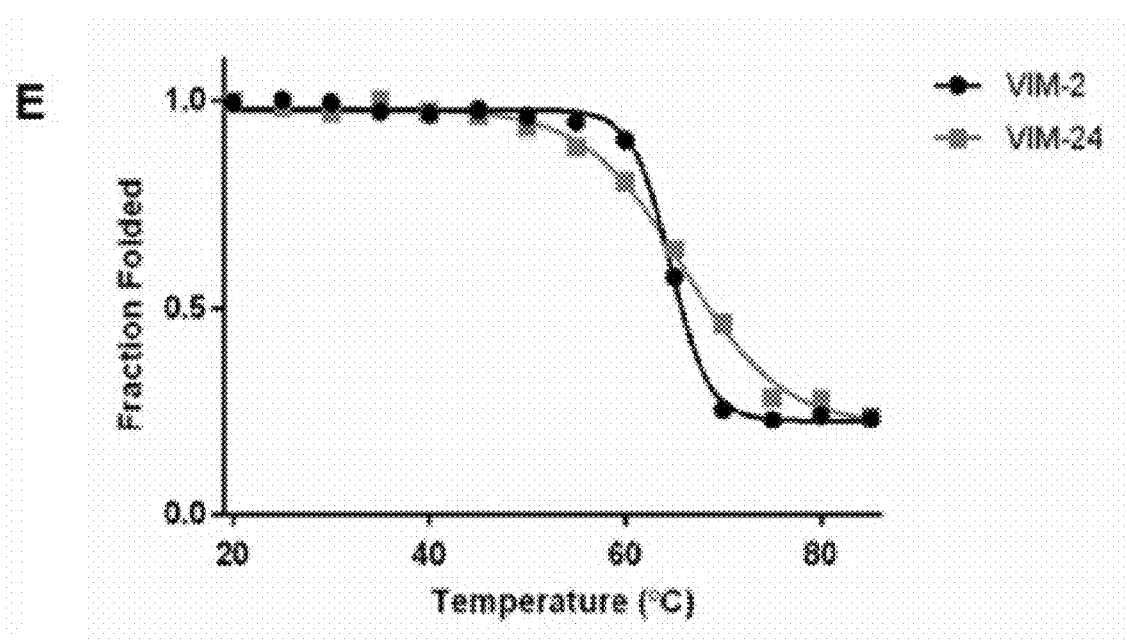
FIGS. 3(A-E) illustrate an immunoblot, mass spectra, and plots characterizing proteins expressed in *E. coli* DH10B and *E. coli* BL21(DE3) pLys cells. Steady-state expression of the R228X library in *E. coli* DH10B was analyzed by immunoblotting. Proteins were detected from whole cell lysates (A). VIM-2 and VIM-24 were overexpressed in *E. coli* BL21 (DE3) pLys cells and analyzed by electrospray ionization mass spectrometry (ESI-MS) and circular dichroism (CD). Mass spectra of purified VIM-2 (B) shows one major peak of 25602±2 amu, which is consistent with cleavage of the leader sequence after residue 25. Mass spectra of purified VIM-24 (C) shows two major peaks of 26206 and 25987±2 amu, which correspond to cleavage after residues 20 and 21, respectively. Far-UV CD spectra of VIM-2 and VIM-24 (D); Thermal denaturation of VIM-2 and VIM-24 followed by ellipticity at 222 nm. Solid lines are best fits to a two-state denaturation model (E).

Since the R228L mutant (VIM-24) was detected in a clinical isolate and thus represents a natural mutation in response to selective pressure, we characterized the consequences of this substitution for VIM structure and function. Purified VIM-2 and VIM-24 both bound approximately 2 $Zn^{2+}$ atoms as measured by the PAR method. Mass spectrometry further confirmed protein identity and revealed one major peak of 25602±2 amu for VIM-2. This value is consistent with cleavage of the protein's leader sequence after residue 25. On the other hand, pure VIM-24 showed two main peaks of 26206 and 25987±2 amu, which corresponds to cleavage after residues 20 (plus an additional Met residue on the N-terminus, as the codon for this residue is introduced with the NdeI restriction site used to clone the gene into the vector) and 21, respectively (FIGS. 3B and 3C). Comparison of the CD scans revealed that VIM-2 and VIM-24 exhibit very similar CD spectra (FIG. 3D). On thermal denaturation, both proteins displayed a single cooperative transition to an unfolded state with calculated $T_m$ values of 62° C. for VIM-2 and 63° C. for VIM-24 (FIG. 3E). However, the unfolding transition for VIM-24 is less steep compared to that for VIM-2, suggesting a more gradual unfolding process. Crystal structures of VIM-2 have revealed that Arg228 hydrogen bonds with a terminally Zn-coordinated water molecule. The presence of this water molecule has been linked to a cooperative metal binding, meaning that the binding of one atom of $Zn^{2+}$ facilitates the binding of the second one. Likewise, the unbinding of one $Zn^{2+}$ leads to the unbinding of the second one which, we hypothesize, results in a faster unfolding process. Since the presence of the Leu residue at position 228 in VIM-24 does not allow the coordination of this terminally Zn-coordinated water molecule, the Zn binding/unbinding process is not cooperative. This may lead to the presence of apo-, mono- and di-zinc forms of the enzyme resulting in a slower unfolding process. Taken together, our results suggest that the R to L substitution does not introduce significant changes to the overall metal or secondary structure content or global stability of the protein.

To better understand the impact of the R228L change upon kinetic behavior, the steady state kinetic parameters of VIM-2 and VIM-24 were determined with a series of substrates. VIM-24 displays a lower catalytic efficiency against the majority of the substrates tested (Table 2). For ampicillin and cephalothin, the decreased $k_{cat}/K_M$ is due to the higher $K_M$ values, with no concomitant change in $k_{cat}$. For imipenem, a lower $k_{cat}$ is observed with little change in $K_M$, consistent with slower turnover. For ceftazidime and cefepime we could not reach saturating concentrations of substrate under the experimental conditions used. However, clear differences were evident in the steady-state hydrolysis of these two substrates by VIM-2 and VIM-24 (FIGS. 4A and 4B) and were manifest in the $k_{cat}/K_M$ ratio calculated by fitting progress curves to Equation 2. For ceftazidime, $k_{cat}/K_M$ was $1\times10^4$ $M^{-1}s^{-1}$ for VIM-2 and $6\times10^4 M^{-1}s^{-1}$ for VIM-24. For cefepime, the values were $3\times10^4$ $M^{-1}s^{-1}$ for VIM-2, and $1\times10^5$ $M^{-1}s^{-1}$ for VIM-24.

by immunoblotting (FIG. 4C), and initial velocities determined at 800 µM cefepime or 400 µM ceftazidime (maximal concentrations at which velocities could be measured). For VIM-24 the rate of cefepime hydrolysis ($5.3\times10^{-7}$ M $s^{-1}$) increased compared to VIM-2 ($2.9\times10^{-7}$ $M^{s-1}$). VIM-24 hydrolyzed ceftazidime at a rate of $4\times10^{-7}$ M $s^{-1}$, whereas measurable rates of hydrolysis were not obtained using VIM-2. These results clearly demonstrate that substitution of Arg for Leu at position 228 changes the substrate specificity of VIM enzymes to favor hydrolysis of 3rd and/or 4th generation cephalosporins.

The VIM-2 R228L Substitution Relieves Steric Clashes with Bound Cephems

In MBLs such as VIM-2 the extended guanidine side chain of Arg228, may replicate the role of Lys224 in interacting with the C3/C4 carboxylate of β-lactam substrates (13, 14), while docking experiments implicate Arg228 (in addition to residues at the ASL-3) in positioning the substrate through interactions with the large, charged C3 substituents (R2 groups) of hydrolyzed cephalosporins such as ceftazidime. For VIM-1, VIM-19, and related enzymes, activity against such substrates may be enhanced by the presence of Ser at position 228 resulting in a more "open" active site. In line with these observations, screening of VIM-2 variants at position 228 identified that small residues (Val, Ala, Ser, Thr, and Gly), and those with nonpolar side chains (Ile and Leu (VIM-24)) all increased the MICs for cefepime and ceftazidime (complete MIC data is provided as supplemental information). We consider the most likely explanation for these findings to be that both steric and charge:charge interactions involving position 228 of the VIM MBLs and the β-lactam R2 substituent group can orient and position substrates within the active site. To test this notion we used the crystal structure of VIM-2 (PDB entry 2YZ3) to derive a molecular model of VIM-24.

A docking of unhydrolyzed cefepime was modeled into the active site of VIM-24 and minimized the resulting complex using YASARA. As shown in FIG. 5, the presence of Leu228 creates an active site groove in VIM-24 large enough to accommodate the bulky C3 N-methylpyrrolidine group of cefepime without requiring significant conformational rearrangement (FIG. 5A). By way of contrast, the guanidinium side chain of VIM-2 Arg228 protrudes suffi-

TABLE 2

Steady-state kinetic data of VIM-2 and VIM-24[a]

| | VIM-2 | | | VIM-24 | | |
|---|---|---|---|---|---|---|
| Substrate | $K_M$ (µM) | $k_{cat}$ ($s^{-1}$) | $k_{cat}/K_M$ ($M^{-1}*s^{-1}$) | $K_M$ (µM) | $K_{cat}$ ($s^{-1}$) | $k_{cat}/KM$ ($M^{-1}*s^{-1}$) |
| Nitrocefin | 13 ± 1 | 430 ± 20 | $3.3 \times 10^7$ | 11 ± 1 | 171 ± 4 | $1.6 \times 10^7$ |
| Ampicillin | 23 ± 4 | 217 ± 9 | $9.9 \times 10^6$ | 97 ± 6 | 217 ± 5 | $2.2 \times 10^6$ |
| Cephalothin | 17 ± 2 | 168 ± 8 | $9.8 \times 10^6$ | 33 ± 5 | 150 ± 9 | $4.5 \times 10^6$ |
| Ceftazidime | NM | NM | $1 \times 10^4$ [b] | NM | NM | $6 \times 10^4$ [b] |
| Cefepime | NM | NM | $3 \times 10^4$ [b] | NM | NM | $1 \times 10^5$ [b] |
| Imipenem | 12 ± 1 | 45 ± 1 | $3.6 \times 10^6$ | 5.0 ± 0.7 | 8.8 ± 0.3 | $1.7 \times 10^6$ |

[a] Values reported are averages ± standard deviations from triplicate experiments.
[b] Calculated from the progress curves of reaction, as described in Experimental Procedures.
NM: not measured.

In order to correlate the MIC results with the kinetic activity of VIM-2 and VIM-24, we measured the hydrolysis of cefepime and ceftazidime in periplasma. Determination of enzymatic activity in periplasma has been shown to parallel the resistance profile, as it more closely resembles conditions in vivo. Periplasmic MBL levels were quantified ciently into the substrate binding cleft to create a clear steric clash (FIG. 5B). In this conformation, the Arg is ≈8 Å away from the carboxylate group of the substrate and completely unable to form any hydrogen bond with it. We anticipate the interaction between Arg228 and the R2 substitution of ceftazidime to be equally unfavorable, not only because the structural similarity, but because in this case the R2 substitution is positively charged. Therefore, we conclude that the shorter Leu side chain facilitates access of both cephems to the active site of VIM-24, increasing turnover of what are still, poor substrates.

BTZs are Slow-Binding Inhibitors of VIM-2 and VIM-24 with Micromolar Affinity

In addition to interacting with substrates (especially cephems), VIM-2 Arg228 is also positioned to form part of a binding site for potential MBL inhibitors. Thus, we investigated the interaction of VIM-2 and VIM-24 with four candidate BTZ inhibitors comprising two pairs of stereoisomers. Interestingly, under steady-state conditions, BTZs were effective inhibitors of both VIM-2 and VIM-24, with observed Ki values (determined using NCF as reporter substrate) between 3.7 and 14 µM (Table 3). All four compounds increased the apparent KM, but exert essentially no effect on kcat, consistent with a competitive mode of inhibition. Although the Ki values were in general slightly higher for VIM-24, the maximal effect was less than two-fold. On this basis we conclude that unlike the effects seen with β-lactams, interaction with Arg228 does not make a major contribution to BTZ affinity for the VIM MBLs. This has significant implication for further development of this class of BTZ inhibitor.

inhibitor binding, $K_i^*$, could be calculated by fitting the final $v_s$ determined at different inhibitor concentrations to equation 6. These values are summarized in Table 3. In agreement with the conclusion that inhibition occurs by a slow binding two-step process, we found that $K_i \gg K_i^*$, as the values of $K_i^*$ were observed to be significantly lower (0.04-0.6 µM) than the $K_i$ values obtained by analysis of the inhibitor dependence of $v_0$ (4-14 µM).

Figure 6B:
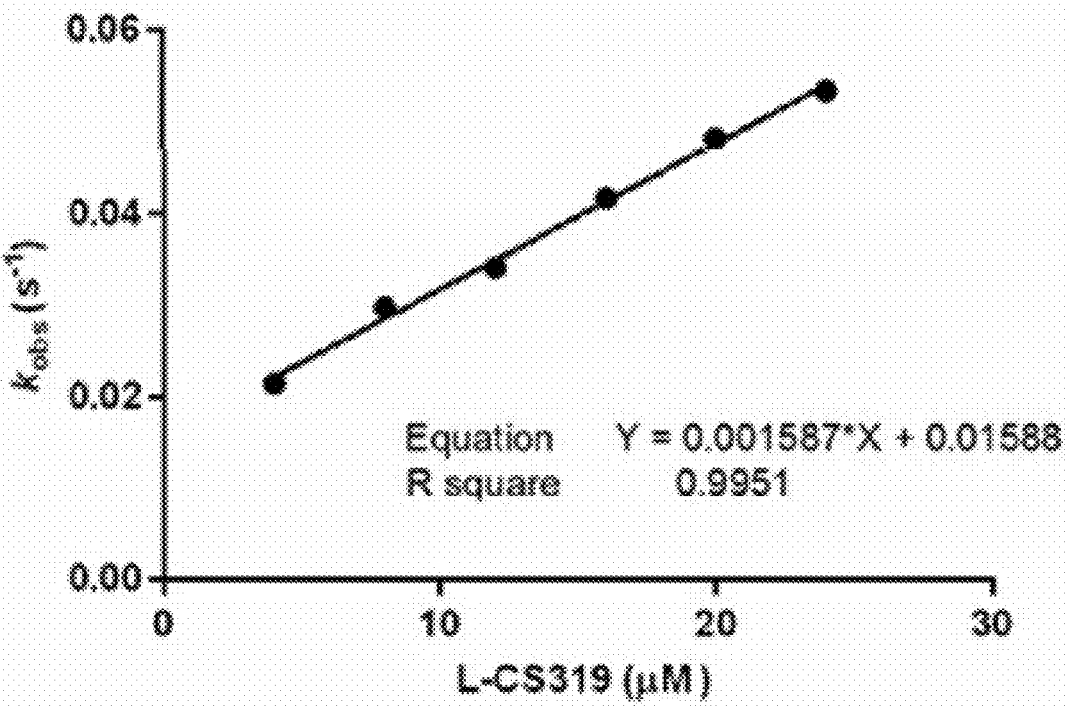
FIGS. 6(A-C) illustrate plots showing BTZ-induced inhibition of hydrolysis. Reaction was initiated by addition of 3 nM of VIM-2 to a mixture of buffer, L-CS319 and 50 µM nitrocefin (A); kobs vs. [I] plot for L-CS319 onset of VIM-2 inhibition. Data were fitted (B); Reaction was initiated by addition of 0.5 nM of VIM-2 pre incubated for 5 min with L-CS319, to a mixture of buffer and 50 µM nitrocefin (C).

For a two-step time-dependent onset of inhibition model, the dependence of $k_{obs}$ on the concentration of inhibitor at limiting [I] reflects the second order rate constant $k_2/K_i^*[I]/(1+S/K_m)$, where $k_2$ is the rate constant for formation of E*I, and $K_i$ is the equilibrium binding constant for the first binding step (Eq. 5). The observed values for $k_2$, estimated from the slope obtained from the plot of the calculated kobs vs. inhibitor concentration, range from 0.01-0.09 s-1 (FIG. 6B). Given the observed values of $K_i$ (4-14 µM) and $K_i^*$ (0.04-0.6 µM) the equilibrium constant for the conformational change step (defined as $K_i'=k_{-2}/k_2$) must lie in the range of 0.1-0.01 for both VIM-2 and VIM-24 (since $K_i^*=K_i/(1+k_2/k_{-2})$. As a consequence of the slow rate constants observed for formation of E*I, the rate constant for breakdown of the E*I complex ($k_2$) is also very slow (Table 3).

TABLE 3

Inhibition of VIM-2 and VIM-24 by BTZs

| | VIM-2 | | | | VIM-24 | | | |
|---|---|---|---|---|---|---|---|---|
| Compound | $K_i$ (µM) | $K_i^*$ (µM) | $k_2$ (s$^{-1}$) | $k_{-2}$ (s$^{-1}$) | $K_i$ (µM) | $K_i$ (µM) | $k_2$ (s-1) | $k_{-2}$ (s$^{-1}$) |
| L-CS319 | 3.7 ± 0.3 | 0.04 ± 0.01 | 0.03 ± 1 × 10$^{-3}$ | 0.0003 ± 1 × 10$^{-4}$ | 6.0 ± 0.7 | 0.12 ± 0.02 | 0.06 ± 2 × 10$^{-3}$ | 0.001 ± 1 × 10$^{-3}$ |
| D-CS319 | 5.4 ± 0.4 | 0.18 ± 0.02 | 0.01 ± 1 × 10$^{-3}$ | 0.0003 ± 1 × 10$^{-4}$ | 11 ± 0.8 | 0.64 ± 0.01 | 0.07 ± 4 × 10$^{-3}$ | 0.004 ± 1 × 10$^{-3}$ |
| L-VC26 | 3.8 ± 0.2 | 0.25 ± 0.01 | 0.02 ± 1 × 10$^{-3}$ | 0.001 ± 1 × 10$^{-3}$ | 4.9 ± 0.3 | 0.13 ± 0.02 | 0.04 ± 2 × 10$^{-3}$ | 0.001 ± 1 × 10$^{-3}$ |
| D-VC26 | 14 ± 1 | 0.10 ± 0.03 | 0.09 ± 4 × 10$^{-3}$ | 0.0006 ± 4 × 10$^{-4}$ | 12 ± 3 | 0.08 ± 0.01 | 0.01 ± 3 × 10$^{-3}$ | 0.00007 ± 1 × 10$^{-5}$ |

More detailed investigations identified that BTZ inhibition of both VIM-2 and VIM-24 arises from a slow-binding two-step process, as previously described for neutral thiol inhibitors of IMP-1, captopril inhibition of angiotensin converting enzyme, and some thiol inactivators of leucine amino peptidase. At increasing inhibitor concentrations NCF hydrolysis proceeds in two phases transitioning from a rapid initial ($v_0$) to a slower steady-state ($v_s$) velocity (FIG. 6A). This behavior is consistent with initial formation of a relatively weak inhibitor complex (EI) that resolves to a more stable species (E*I) during the course of the reaction. According to this model of inhibition, $K_i$ is the measure of the affinity of the initial complex, EI, whereas the true overall dissociation constant of an inhibitor that conforms to this mechanism is defined by the dissociation constant for the final high-affinity conformation of the enzyme inhibitor complex $K_i^*$ ($K_i^*=K_i/(1+(k_2/k_{-2}))$).

Figure 6C:
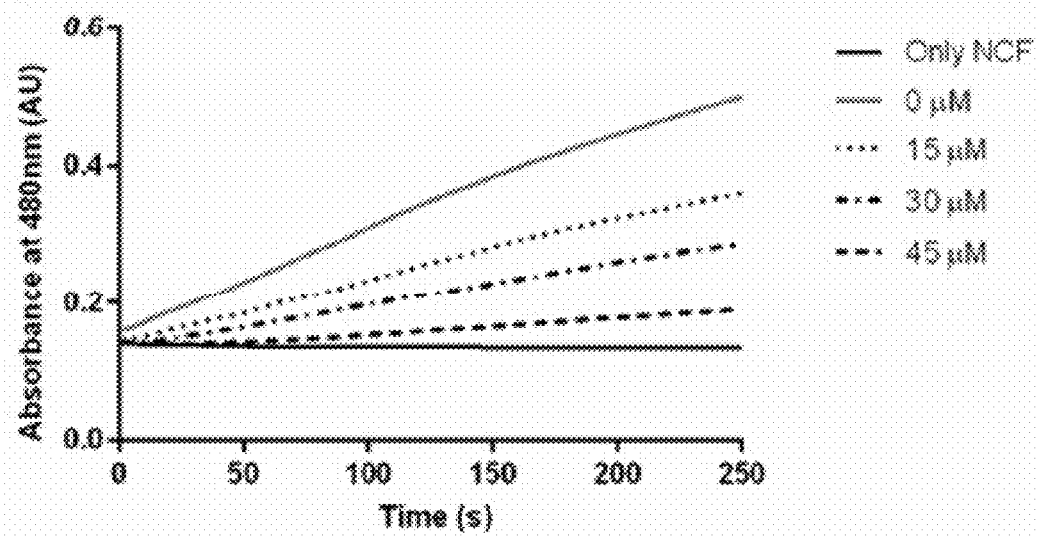

To verify that this model correctly describes the observed behavior, the kinetic data were fitted to alternative models. The best fit was obtained with a two-step model where both $v_0$ and $v_s$ decrease with increasing inhibitor concentration (FIG. 6A), as evidenced by a more consistent fit to the data, and narrower 95% confidence intervals, than could be obtained with a simpler, one-step scheme where v0 did not vary with inhibitor concentration (statistical analysis for the fitting of L-CS319-induced inhibition of NCF hydrolysis by VIM-2 is provided as supplemental information). From these data the overall equilibrium dissociation constant for To further test this model, the kinetics of reactions in which the enzyme was preincubated with inhibitor prior to the addition of substrate were analyzed. For a time-dependent onset of inhibition mechanism, a pre-incubation step should eliminate the biphasic kinetics observed in reactions where inhibitor and substrate are added at the same time. Consistent with this conclusion, reactions after pre-incubation of enzyme and inhibitor show simple, linear, steady-state kinetics. Moreover, the observed initial rates obtained from enzyme pre-incubated with inhibitor are consistent with the tighter inhibitor binding constant $K_i^*$ (FIG. 6C and Table 3). Taken together, the kinetic data are consistent with a model in which rapid but relatively weak binding of the inhibitor in the substrate-binding pocket is followed by conformational changes to a more stable enzyme-inhibitor complex.

Crystallography Reveals Key Interactions Between VIM-2 and L-CS319

To further investigate the interaction of VIM enzymes and BTZ inhibitors, we sought to obtain a crystal structure for a BTZ:VIM-2 complex. Initial experiments soaking the most potent inhibitor, L-CS319, into a previously described VIM-2 crystal form failed to yield interpretable electron density. Hence we used co-crystallization to generate a new crystal form (space group P21, 2 molecules in the asymmetric unit; Table 4), diffracting to near-atomic resolution (1.25 Å). The structure was solved by molecular replacement and refined as described, with the final model containing 230 and 234 amino acids in chains A and B, respectively.

TABLE 4

Crystallographic Data Collection and Refinement Statistics

| | |
|---|---|
| Dataset | VIM-2:CS319 |
| Processing | XDS/SCALA |
| Beamline | DLS I04-1 |
| Space Group | P $2_1$ |
| Cell Dimensions (Å) | a = 52.89 b = 61.40 c = 68.92 β = 100.9° |
| Wavelength (Å) | 0.9200 |
| Resolution (Å)[a] | 29.64-1.25 (1.32-1.25) |
| Total reflections[a] | 302 755 (38 004) |
| Unique reflections[a] | 115 461 (15 946) |
| Completeness (%)[a] | 96.7 (91.8) |
| Redundancy[a] | 2.6 (2.4) |
| I/(sig. I)[a] | 11.1 (2.3) |
| Rmerge (%)[a] | 0.040 (0.395) |
| Refinement | REFMAC5 |
| Total reflections | 109 653 |
| Resolution (Å) | 29.64-1.25 |
| Rcryst (%) Rfree (%)[b] | 14.5 16.4 |
| RMS bond length (Å) | 0.0064 |
| RMS bond angle (Å) | 1.4591 |
| Protein atoms | 3578 |
| Water molecules | 355 |
| % residues in Ramachandran regions (favored/allowed/disallowed) | 98.5/1.5/0 |
| Wilson B-factor | 11.3 |
| B-factors (protein) | 15.6 (15.4, 16.0)[c] |
| B-factors (ligand) | 26.7[d], 22.7[e], 14.7[f] |
| B-factors (water molecules) | 27.6 |
| PDB accession code | 4UA4 |

[a]Data for the highest resolution shell are in parentheses.
[b]$R_{free}$ was calculated with 5% of the reflections omitted.
[c]Values for chains A and B respectively.
[d]Major conformation, chain B (occupancy 0.6)
[e]Minor conformation, chain B (occupancy 0.3)
[f]Dimer, chain A.

Difference electron density maps gave clear evidence of bound ligand in both molecules of the asymmetric unit, but showed the nature of the ligand to differ between the two subunits. In molecule A, high-quality electron density extending along the active site groove indicated a ligand significantly larger than a single L-CS319 molecule that was modeled as a dimeric species with two L-CS319 monomers connected by a disulfide bond. However, as assays in solution demonstrated that prolonged exposure to oxidative conditions abolishes the inhibitory activity of L-CS319 and other BTZs towards MBLs (data not shown), we conclude that this is most likely an artifact structure generated by oxidation of the L-CS319 ligand during crystallization, and does not represent the inhibitory VIM-2:L-CS319 complex.

In contrast, the active site of molecule B contained positive electron density of a size and shape expected for a monomer of L-CS319. Although this positive density was more diffuse than would be expected at this resolution, a strong peak between the two zinc ions was considered to indicate the inhibitor thiol group in the "bridging" position, and a second strong peak close to the Asn233 backbone amide the inhibitor carboxylate. On this basis L-CS319 could be fitted into the difference map and refined with occupancy of 0.6 (Table 4). However, the best results were obtained when a second inhibitor molecule, with occupancy of 0.3, was fitted into the additional diffuse electron density. This low-occupancy conformation shares a common location for the carboxylate group, but differs in the precise orientation of the BTZ core and in the positioning of the thiol, which notably is not intercalated between the two $Zn^{2+}$ ions. The description below focuses on the high-occupancy conformation. We note however that observation of two conformations for bound L-CS319 in the crystal structure is consistent with the presence of multiple enzyme:inhibitor complexes in solution as observed in the inhibition assays above.

L-CS319 is positioned with the BTZ ring system lying at approximately 45° to the floor of the active site groove. Key interactions with VIM-2 involve the thiol, which adopts the bridging position between the two zinc ions seen in other MBL:thiol complexes (for example, phenylC3SH, rhodanine, and Tiopronin); and the carboxylate, which forms hydrogen bonds to the Asn233 backbone amide nitrogen and to a bound water molecule that is positioned by the Cys221 backbone carbonyl. Notably, the inhibitor carboxylate is too far from the Zn2 (Cys-His-Asp site) metal ion to make a direct interaction, unlike the situation for complexes of other B1 MBLs with hydrolyzed β-lactams. Interestingly, although the Arg228 guanidino moiety is within hydrogen bonding distance of the inhibitor carboxylate, the two groups are not well oriented for interaction. Weak electron density for the Arg228 guanidino group, which was refined in two conformations, also argues against a strong interaction between this residue and bound inhibitor. This apparent lack of involvement of Arg228 in BTZ binding is consistent with the similar levels of BTZ inhibition of VIM-2 and VIM-24, supporting the conclusion that Arg228 does not substantially contribute to inhibitor affinity. L-CS319 binding does involve hydrophobic contacts, namely edge:face interactions between the two rings of the fused BTZ system and the side chains of Phe61 and Tyr67 at the base of the Active Site Loop 3 (ASL3; residues 60 to 67), and with the more distant side chain of the conserved Trp87. In addition the side chain of the zinc ligand His263, sits beneath and approximately parallel to the inhibitor scaffold.

The overall conformation of VIM-2 in the L-CS319 complex differs little from that of the free enzyme and complexes with mercaptocarboxylate and rhodanine inhibitors. The main differences are in ASL3, which adapts its position, in particular the orientation of the Phe61 side chain, to accommodate the different inhibitors. However, these differences are far less marked than in ligand complexes of other B1 enzymes, such as IMP-1 or NDM-1, where much more profound changes in ASL3 conformation have been observed. This may arise from the location of aromatic residues likely to be important to ligand binding at the base of the VIM ASL3 (Phe61 and Tyr67) rather than at its apex, as is the case for Trp64 or Phe64 in the IMP and NDM MBLs, respectively. Repositioning of the side chain at position 64 on ligand binding is likely to require much greater movement of the ASL3 in both of these enzymes. Comparison of the mode of binding of L-CS319 and the rhodanine fragment ML302F shows that the bridging thiol, multiple conformations for the Arg228 side chain, and interactions with the Asn233 backbone amide and the Cys221-bound water molecule are common to binding of both inhibitors. As this water molecule is present in an identical position in all but one available VIM-2 structures, while the conformation of the Arg228 side chain varies, it is possible that in VIM-2 it is this water molecule, rather than Arg228, that makes the major contribution to binding the C3/C4 carboxylate of β-lactam substrates and thus replicates the role of Lys224 in other B1 MBLs.

BTZs Restore Imipenem Activity Against VIM-2 and VIM-24 Producing Gram-Negative Pathogens To assess the capacity of the BTZ inhibitors to restore efficacy of imipenem, we performed microbiological assays using two clinical isolates: VIM-2 harboring *P. aeruginosa* (imipenem MIC=32 µg/ml) and VIM-24 producing *K. pneumoniae* (imipenem MIC=1 µg/ml). Viable cell counts following exposure to sub-lethal concentrations of imipenem in the presence of inhibitors (FIG. 7) showed that the BTZs are able to inhibit both MBLs within bacteria, as evidenced by the significant reductions in bacterial count (p-values<0.05). The inhibitors do not have any antimicrobial effect on their own, as differences could not be detected in viable cell number between BTZ-exposed cells and broth only controls (data not shown).

While this invention has been particularly shown and described with references to preferred embodiments thereof, it will be understood by those skilled in the art that various changes in form and details may be made therein without departing from the scope of the invention encompassed by the appended claims. All patents, publications and references cited in the foregoing specification are herein incorporated by reference in their entirety.

Having described the invention, we claim:

1. A method of treating a bacterial infection in a subject in need thereof, the method comprising:
   administering to the subject therapeutically effective amounts of at least one β-lactam antibiotic and at least one bisthiazolidine or fused oxazolidine metallo-β-lactamase-inhibitor wherein the fused oxazolidine is a compound of formula (II).

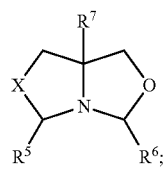

(II)

wherein x is O or S,
  $R^5$ is selected from the group consisting of a substituted or unsubstituted $C_1$-$C_{12}$ alkylthio, $C_1$-$C_{12}$ alkyldithio $C_1$-$C_{12}$ alkylsulfonyl, and $C_1$-$C_{12}$ alkylsulfate;
  $R^6$ and $R^7$ are each independently selected from the group consisting of H, a substituted or unsubstituted carboxy, $C_1$-$C_{12}$ alkyl, carboxylato, carbamoyl, $C_1$-$C_{12}$ alcohol, $C_1$-$C_{12}$ alkoxycarbonyl, $C_1$-$C_{12}$ alkylcarbonato, $C_1$-$C_{12}$ alkyl-carbamoyl, and hydroxyaminocarbonyl; and pharmaceutically acceptable salts thereof.

2. The method of claim 1, wherein the bisthiazolidine or fused oxazolidine metallo-β-lactamase inhibitor comprises a compound having the formula:

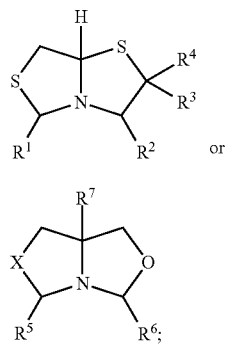

(I)

or (II)

wherein x is O or S,
  $R^1$ is selected from the group consisting of a substituted or unsubstituted $C_1$-$C_{12}$ alkylthio, $C_1$-$C_{12}$ alkyldithio, $C_1$-$C_{12}$ alkylsulfonyl, and $C_1$-$C_{12}$ alkylsulfate, $R^2$ is selected from the group consisting of H, a substituted or unsubstituted carboxy, $C^1$-$C^{12}$ alkyl, $C^1$-$C^{12}$ alkenyl, carboxylato, carbamoyl, $C^1$-$C^{12}$ alcohol, $C^1$-$C^{12}$ alkoxycarbonyl, $C_1$-$C_5$ alkylcarbonato, $C_1$-$C_5$ alkyl-carbamoyl, and hydroxyaminocarbonyl, $R^3$ and $R^4$ are each independently selected from the group consisting of a H, a $C_1$-$C_{12}$ alkyl, and $C_1$-$C_{12}$ alkenyl, and wherein $R^2$ and $R^3$ may be linked to form a cyclic or polycyclic ring,
  $R^5$ is selected from the group consisting of a substituted or unsubstituted $C_1$-$C_{12}$ alkylthio, $C_1$-$C_{12}$ alkyldithio $C_1$-$C_{12}$ alkylsulfonyl, and $C_1$-$C_{12}$ alkylsulfate;
  $R^6$ and $R^7$ are each independently selected from the group consisting of H, a substituted or unsubstituted carboxy, $C_1$-$C_{12}$ alkyl, carboxylato, carbamoyl, $C_1$-$C_{12}$ alcohol, $C_1$-$C_{12}$ alkoxycarbonyl, $C_1$-$C_{12}$ alkylcarbonato, $C_1$-$C_{12}$ alkyl-carbamoyl, and hydroxyaminocarbonyl; and pharmaceutically acceptable salts thereof.

3. The method of claim 1, wherein the bacterial infection is a carbapenem resistant gram negative bacterial infection.

4. The method of claim 3, wherein the bisthiazolidine or fused oxazolidine metallo-β-lactamase inhibitor is administered to the subject at an amount effective to inhibit carbapenemase or carbapenem-hydrolyzing β-lactamase activity.

5. The method of claim 1, wherein the bisthiazolidine metallo-β-lactamase inhibitor comprises at least one compound having the formula:

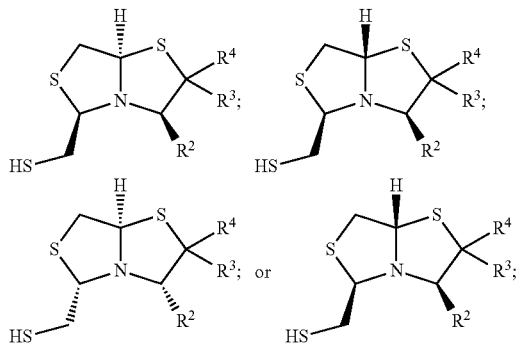

$R^2$ is selected from the group consisting of H, a substituted or unsubstituted carboxy, $C_1$-$C_{12}$ alkyl, $C_1$-$C_{12}$ alkenyl, carboxylato, carbamoyl, $C_1$-$C_{12}$ alcohol, $C_1$-$C_{12}$ alkoxycarbonyl, $C_1$-$C_5$ alkylcarbonato, $C_1$-$C_5$ alkyl-carbamoyl, and hydroxyaminocarbonyl,
  $R^3$ and $R^4$ are each independently selected from the group consisting of a H, a $C_1$-$C_{12}$ alkyl, and $C_1$-$C_{12}$ alkenyl, and wherein $R^2$ and $R^3$ may be linked to form a cyclic or polycyclic ring, and pharmaceutically acceptable salts thereof.

6. The method of claim 1, wherein the bisthiazolidine metallo-β-lactamase inhibitor comprises at least one compound having the formula:

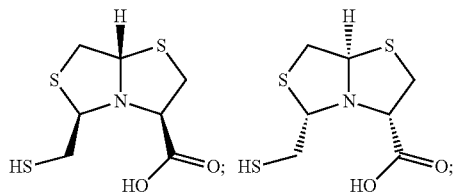

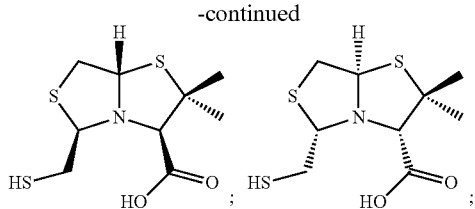

and pharmaceutically acceptable salts thereof.

7. The method of claim 1, wherein the β-lactam antibiotic comprises at least one of amoxicillin, ampicillin, azlocillin, mezlocillin, hetacillin, bacampicillin, carbenicillin, sulbenicillin, ticarcillin, piperacillin, mecillinam, methicillin, ciclacillin, oxacillin, cloxacillin, dicloxacillin, nafcillin, cephalothin, cephaloridine, cefaclor, cefadroxil, cefamandole, cefazolin, cephalexin, cephradine, ceftizoxime, cefoxitin, cephacetrile, cefotiam, cefotaxime, cefsulodin, cefoperazone, cefinenoxime, cefmetazole, cephaloglycin, cefonicid, cefodizime, cefpirome, ceftazidime, ceftriaxone, cefpiramide, cefozopran, cefepime, cefuzonam, cefpimizole, cefclidin, cefixime, ceftibuten, cefdinir, cefpodoxime axetil, cefpodoxime proxetil, cefteram pivoxil, cefetamet pivoxil, cefcapene pivoxil, cefditoren pivoxil, cefuroxime, cefuroxime axetil, loracarbacef, latamoxef, CXA-101, imipenem, meropenem, biapenem, panipenem, ertapenem, doripenem, aztreonam, carumonam, and pharmaceutically acceptable salts.

8. A method of treating a β-lactam resistant bacterial infection in a subject in need thereof, the method comprising:
administering to the subject therapeutically effective amounts of at least one β-lactam antibiotic and at least one bisthiazolidine or fused oxazolidine metallo-β-lactamase-inhibitor, wherein the bisthiazolidine or fused oxazolidine metallo-β-lactamase inhibitor having the formula:

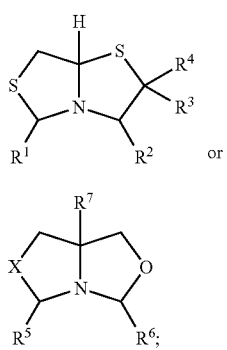

Wherein x is O or S,
$R^1$ is selected from the group consisting of a substituted or unsubstituted $C_1$-$C_{12}$ alkylthio, $C_1$-$C_{12}$ alkyldithio, $C_1$-$C_{12}$ alkylsulfonyl, and $C_1$-$C_{12}$ alkylsulfate,
$R^2$ is selected from the group consisting of H, a substituted or unsubstituted carboxy, $C_1$-$C_{12}$ alkyl, $C_1$-$C_{12}$ alkenyl, carboxylato, carbamoyl, $C_1$-$C_{12}$ alcohol, $C_1$-$C_{12}$ alkoxycarbonyl, $C_1$-$C_5$ alkylcarbonato, $C_1$-$C_5$ alkyl-carbamoyl, and hydroxyaminocarbonyl,
$R^3$ and $R^4$ are each independently selected from the group consisting of a H, a $C_1$-$C_{12}$ alkyl, and $C_1$-$C_{12}$ alkenyl, and wherein $R^2$ and $R^3$ may be linked to form a cyclic or polycyclic ring, $R^5$ is selected from the group consisting of a substituted or unsubstituted $C_1$-$C_{12}$ alkylthio, $C_1$-$C_{12}$ alkyldithio $C_1$-$C_{12}$ alkylsulfonyl, and $C_1$-$C_{12}$ alkylsulfate;
$R^6$ and $R^7$ are each independently selected from the group consisting of H, a substituted or unsubstituted carboxy, $C_1$-$C_{12}$ alkyl, carboxylato, carbamoyl, $C_1$-$C_{12}$ alcohol, $C_1$-$C_{12}$ alkoxycarbonyl, $C_1$-$C_{12}$ alkylcarbonato, $C_1$-$C_{12}$ alkyl-carbamoyl, and hydroxyaminocarbonyl; and pharmaceutically acceptable salts thereof.

9. The method of claim 8, wherein the bacterial infection is a carbapenem resistant gram negative bacterial infection.

10. The method of claim 9, wherein the bisthiazolidine or fused oxazolidine metallo-β-lactamase inhibitor is administered to the subject at an amount effective to inhibit carbapenemase or carbapenem-hydrolyzing β-lactamase activity.

11. The method of claim 8, wherein the bisthiazolidine metallo-β-lactamase inhibitor comprises at least one compound having the formula:

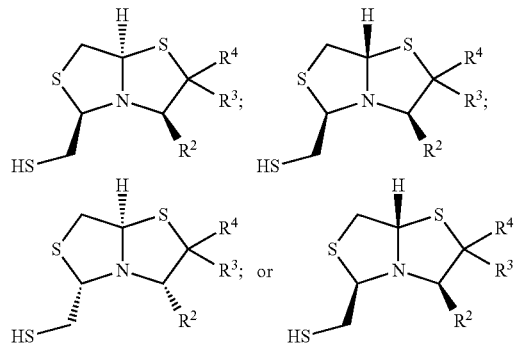

$R^2$ is selected from the group consisting of H, a substituted or unsubstituted carboxy, $C_1$-$C_{12}$ alkyl, $C_1$-$C_{12}$ alkenyl, carboxylato, carbamoyl, $C_1$-$C_{12}$ alcohol, $C_1$-$C_{12}$ alkoxycarbonyl, $C_1$-$C_5$ alkylcarbonato, $C_1$-$C_5$ alkyl-carbamoyl, and hydroxyaminocarbonyl,
$R^3$ and $R^4$ are each independently selected from the group consisting of a H, a $C_1$-$C_{12}$ alkyl, and $C_1$-$C_{12}$ alkenyl, and wherein $R^2$ and $R^3$ may be linked to form a cyclic or polycyclic ring, and pharmaceutically acceptable salts thereof.

12. The method of claim 8, wherein the bisthiazolidine metallo-β-lactamase inhibitor comprises at least one compound having the formula:

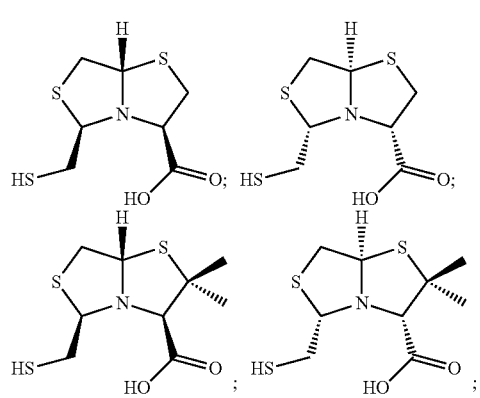

and pharmaceutically acceptable salts thereof.

13. The method of claim 8, wherein the β-lactam antibiotic comprises at least one of amoxicillin, ampicillin, azlocillin, mezlocillin, hetacillin, bacampicillin, carbenicillin, sulbenicillin, ticarcillin, piperacillin, mecillinam, methicillin, ciclacillin, oxacillin, cloxacillin, dicloxacillin, nafcillin, cephalothin, cephaloridine, cefaclor, cefadroxil, cefamandole, cefazolin, cephalexin, cephradine, ceftizoxime, cefoxitin, cephacetrile, cefotiam, cefotaxime, cefsulodin, cefoperazone, cefmenoxime, cefmetazole, cephaloglycin, cefonicid, cefodizime, cefpirome, ceftazidime, ceftriaxone, cefpiramide, cefozopran, cefepime, cefuzonam, cefpimizole, cefclidin, cefixime, ceftibuten, cefdinir, cefpodoxime axetil, cefpodoxime proxetil, cefteram pivoxil, cefetamet pivoxil, cefcapene pivoxil, cefditoren pivoxil, cefuroxime, cefuroxime axetil, loracarbacef, latamoxef, CXA-101, imipenem, meropenem, biapenem, panipenem, ertapenem, doripenem, aztreonam, carumonam, and pharmaceutically acceptable salts.

14. A pharmaceutical composition comprising therapeutically effective amounts of at least one β-lactam antibiotic and at least one bisthiazolidine or fused oxazolidine metallo-β-lactamase inhibitor wherein the fused oxazolidine is a compound of formula (II)

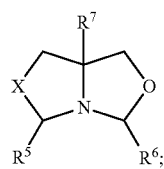

(II)

wherein x is O or S,
R⁵ is selected from the group consisting of a substituted or unsubstituted $C_1$-$C_{12}$ alkylthio, $C_1$-$C_{12}$ alkyldithio $C_1$-$C_{12}$ alkylsulfonyl, and $C_1$-$C_{12}$ alkylsulfate;
R⁶ and R⁷ are each independently selected from the group consisting of H, a substituted or unsubstituted carboxy, $C_1$-$C_{12}$ alkyl, carboxylato, carbamoyl, $C_1$-$C_{12}$ alcohol, $C_1$-$C_{12}$ alkoxycarbonyl, $C_1$-$C_{12}$ alkylcarbonato, $C_1$-$C_{12}$ alkyl-carbamoyl, and hydroxyaminocarbonyl; and pharmaceutically acceptable salts thereof.

15. The composition of claim 14, wherein the bisthiazolidine or fused oxazolidine metallo-β-lactamase inhibitor comprises at least one compound having the formula:

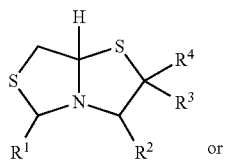

(I)

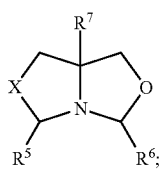

(II)

Wherein x is O or S,
R¹ is selected from the group consisting of a substituted or unsubstituted $C_1$-$C_{12}$ alkylthio, $C_1$-$C_{12}$ alkyldithio, $C_1$-$C_{12}$ alkylsulfonyl, and $C_1$-$C_{12}$ alkylsulfate,
R² is selected from the group consisting of H, a substituted or unsubstituted carboxy, $C_1$-$C_{12}$ alkyl, $C_1$-$C_{12}$ alkenyl, carboxylato, carbamoyl, $C_1$-$C_{12}$ alcohol, $C_1$-$C_{12}$ alkoxycarbonyl, $C_1$-$C_5$ alkylcarbonato, $C_1$-$C_5$ alkyl-carbamoyl, and hydroxyaminocarbonyl,
R³ and R⁴ are each independently selected from the group consisting of a H, a $C_1$-$C_{12}$ alkyl, and $C_1$-$C_{12}$ alkenyl, and wherein R² and R³ may be linked to form a cyclic or polycyclic ring,
R⁵ is selected from the group consisting of a substituted or unsubstituted $C_1$-$C_{12}$ alkylthio, $C_1$-$C_{12}$ alkyldithio $C_1$-$C_{12}$ alkylsulfonyl, and $C_1$-$C_{12}$ alkylsulfate;
R⁶ and R⁷ are each independently selected from the group consisting of H, a substituted or unsubstituted carboxy, $C_1$-$C_{12}$ alkyl, carboxylato, carbamoyl, $C_1$-$C_{12}$ alcohol, $C_1$-$C_{12}$ alkoxycarbonyl, $C_1$-$C_{12}$ alkylcarbonato, $C_1$-$C_{12}$ alkyl-carbamoyl, and hydroxyaminocarbonyl; and pharmaceutically acceptable salts thereof.

16. The composition of claim 14, wherein the therapeutically effective amount of the bisthiazolidine or fused oxazolidine metallo-β-lactamase inhibitor is an amount effective to inhibit carbapenemase or carbapenem-hydrolyzing β-lactamase activity in a subject having a carbapenem resistant gram negative bacterial infection.

17. The composition of claim 14, wherein the bisthiazolidine metallo-β-lactamase inhibitor comprises at least one compound having the formula:

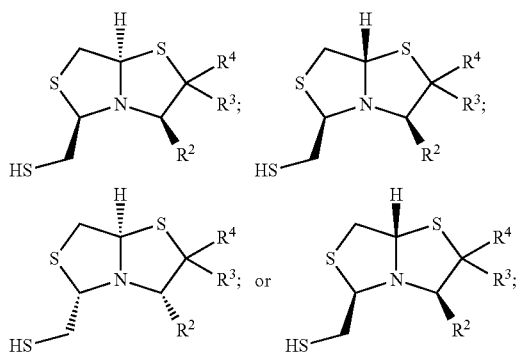

R² is selected from the group consisting of H, a substituted or unsubstituted carboxy, $C_1$-$C_{12}$ alkyl, $C_1$-$C_{12}$ alkenyl, carboxylato, carbamoyl, $C_1$-$C_{12}$ alcohol, $C_1$-$C_{12}$ alkoxycarbonyl, $C_1$-$C_5$ alkylcarbonato, $C_1$-$C_5$ alkyl-carbamoyl, and hydroxyaminocarbonyl,
R³ and R⁴ are each independently selected from the group consisting of a H, a $C_1$-$C_{12}$ alkyl, and $C_1$-$C_{12}$ alkenyl, and wherein R² and R³ may be linked to form a cyclic or polycyclic ring, and pharmaceutically acceptable salts thereof.

18. The composition of claim 14, wherein the bisthiazolidine metallo-β-lactamase inhibitor comprises at least one compound having the formula:

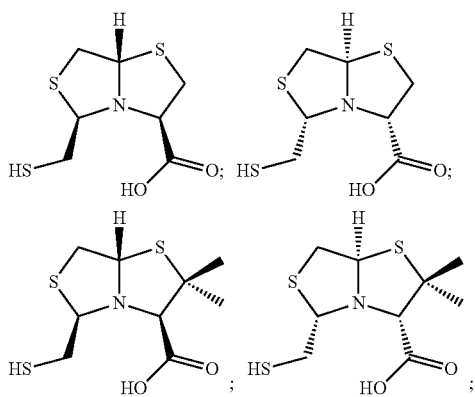

and pharmaceutically acceptable salts thereof.

19. The composition of claim 14, wherein the β-lactam antibiotic comprises at least one of amoxicillin, ampicillin, azlocillin, mezlocillin, hetacillin, bacampicillin, carbenicillin, sulbenicillin, ticarcillin, piperacillin, mecillinam, methicillin, ciclacillin, oxacillin, cloxacillin, dicloxacillin, nafcillin, cephalothin, cephaloridine, cefaclor, cefadroxil, cefamandole, cefazolin, cephalexin, cephradine, ceftizoxime, cefoxitin, cephacetrile, cefotiam, cefotaxime, cefsulodin, cefoperazone, cefmenoxime, cefmetazole, cephaloglycin, cefonicid, cefodizime, cefpirome, ceftazidime, ceftriaxone, cefpiramide, cefozopran, cefepime, cefuzonam, cefpimizole, cefclidin, cefixime, ceftibuten, cefdinir, cefpodoxime axetil, cefpodoxime proxetil, cefteram pivoxil, cefetamet pivoxil, cefcapene pivoxil, cefditoren pivoxil, cefuroxime, cefuroxime axetil, loracarbacef, latamoxef, CXA-101, imipenem, meropenem, biapenem, panipenem, ertapenem, doripenem, aztreonam, carumonam, and pharmaceutically acceptable salts.

* * * * *